(12) United States Patent
Nesterov-Mueller et al.

(10) Patent No.: US 10,376,858 B2
(45) Date of Patent: Aug. 13, 2019

(54) ULTRA HIGH-DENSITY OLIGOMER ARRAYS AND METHOD OF PRODUCTION THEREOF

(71) Applicant: Karlsruher Institut fuer Technologie, Karlsruhe (DE)

(72) Inventors: Alexander Nesterov-Mueller, Pillipsburg (DE); Valentina Bykovskaya, Karlsruhe (DE); Clemens Matthias von Bojnicic-Kninski, Karlsruhe (DE); Felix Friedrich Loeffler, Heidelberg (DE); Roman Popov, Karlsruhe (DE); Barbara Ridder, Ubstadt-Weiher (DE); Frank Breitling, Heidelberg (DE); Daniela Silke Althuon, Karlsruhe (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 0 days.

(21) Appl. No.: 15/951,986

(22) Filed: Apr. 12, 2018

(65) Prior Publication Data
US 2018/0229204 A1   Aug. 16, 2018

Related U.S. Application Data

(63) Continuation of application No. PCT/EP2016/074542, filed on Oct. 13, 2016.

(30) Foreign Application Priority Data

Oct. 15, 2015  (DE) ........................ 10 2015 117 567

(51) Int. Cl.
| | | |
|---|---|---|
| B01J 19/00 | (2006.01) | |
| C07K 1/04 | (2006.01) | |
| G01N 33/68 | (2006.01) | |

(52) U.S. Cl.
CPC ........... B01J 19/0046 (2013.01); C07K 1/047 (2013.01); G01N 33/6854 (2013.01); *B01J 2219/00576* (2013.01); *B01J 2219/00585* (2013.01); *B01J 2219/00596* (2013.01); *B01J 2219/00621* (2013.01); *B01J 2219/00626* (2013.01); *B01J 2219/00711* (2013.01); *B01J 2219/00725* (2013.01)

(58) Field of Classification Search
None
See application file for complete search history.

(56) References Cited

U.S. PATENT DOCUMENTS

| | | |
|---|---|---|
| 6,319,668 B1 | 11/2001 | Nova et al. |
| 2002/0006672 A1 | 1/2002 | Poutska et al. |
| 2005/0089470 A1* | 4/2005 | Johnson ............. A61K 49/0002 424/1.11 |
| 2016/0082406 A1 | 3/2016 | Markle et al. |

FOREIGN PATENT DOCUMENTS

| | | |
|---|---|---|
| DE | 101 56 329 | 2/2003 |
| JP | 37583 | * 2/2012 |
| WO | WO 2015/066400 | 5/2015 |

OTHER PUBLICATIONS

Beyer et al (2007 Science 318:1888 supporting material) (Year: 2007).*
International Preliminary Report on Patentability and Written Opinion, with English-language translation, from International Application No. PCT/EP2016/074542, 16 pages (dated Apr. 26, 2018).
B. Merrifield, "Solid Phase Peptide Synthesis. I. The Synthesis of a Tetrapeptide" *J. Am. Chem. Soc.*, vol. 85:2149-2154 (1963).
Colombo et al. "4-Chloromethylphenoxyacetyl polystyrene and polyamide supports for solid-phase peptide synthesis" *International Journal of Peptide and Protein Research*, vol. 21:118-126 (1983).
Smith "Filamentous fusion phage—novel expression vectors that display cloned antigens on the virion surface" *Science*, vol. 228:1315-1317 (1985).
Fodor et al. "Light-directed, spatially addressable parallel chemical synthesis" *Science*, vol. 251:767-773 (1991).
Yadong et al. "Template-Assisted Self-Assembly: A Practical Route to Complex Aggregates of Monodispersed Colloids with Well-Defined Sizes, Shapes, and Structures" *J. Am. Chem. Soc.*, vol. 123:8718-8729 (2001).
Pellois et al. "Individually addressable parallel peptide synthesis on microchips" *Nature Biotechnology*, vol. 20:922-926 (2002).
Gunderson et al. *Genome Research*, vol. 14(5):870-877 (2004).
Beyer et al. "Combinatorial Synthesis of Peptide Arrays onto a Microchip" *Science*, vol. 318(5858):1888 (2007).
Maerkle et al. "High-Density Peptide Arrays with Combinatorial Laser Fusing" *Advanced Materials*, vol. 26:3730-3734 (2014).
Legutki et al. "Scalable high-density peptide arrays for comprehensive health monitoring" *Nat. Commun.*, vol. 5:4785 (2014).
Nesterov-Mueller et al. "Particle-Based Microarrays of Oligonucleotides and Oligopeptides" *Microarrays*, vol. 3(4):245-262 (2014).

* cited by examiner

*Primary Examiner* — Christopher M Gross
(74) *Attorney, Agent, or Firm* — Klarquist Sparkman, LLP

(57) ABSTRACT

The present invention relates to a method of producing an oligomer array. The invention comprises the steps of: providing a substrate with a multitude of recesses; introducing a first particle with a first molecule into a recess; releasing the first molecule from the first particle; binding the first molecule to a second molecule to form an oligomer while immobilizing the second molecule in the recess; optionally repeating the steps, wherein at least one of the first particles and/or the first molecules comprises a detectable marker.

12 Claims, 9 Drawing Sheets
Specification includes a Sequence Listing.

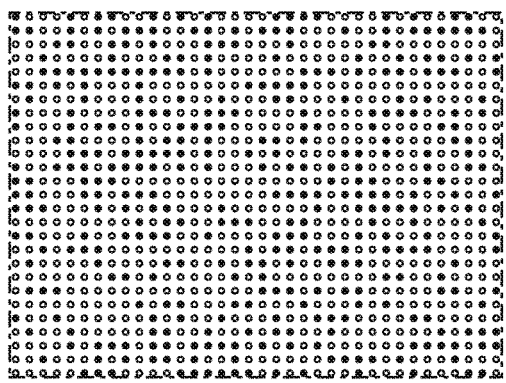 
Fig. 7a                    Fig. 7b
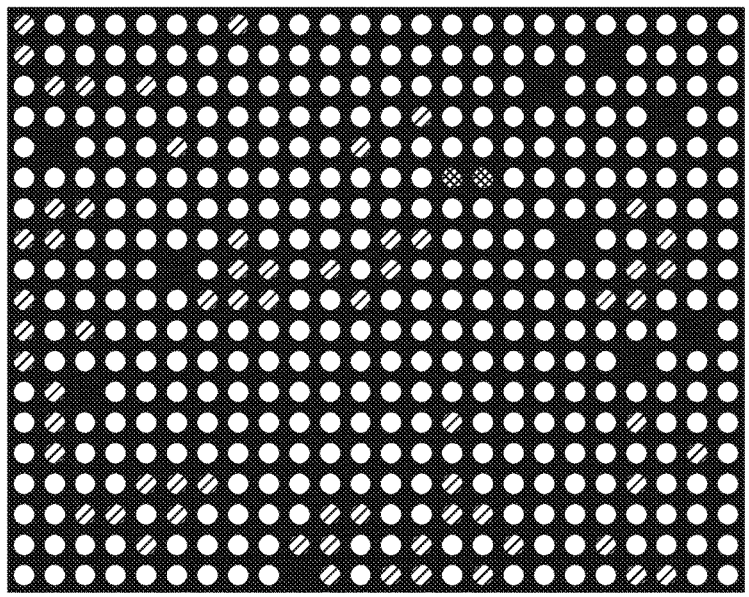
Fig. 8

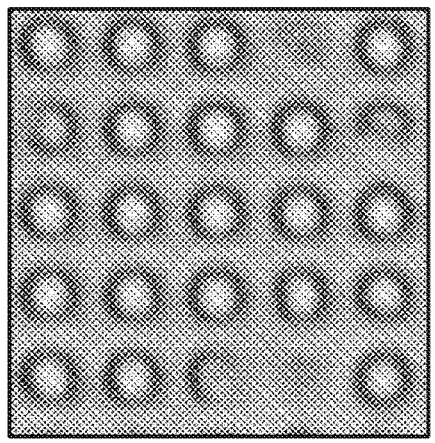
Fig. 9a
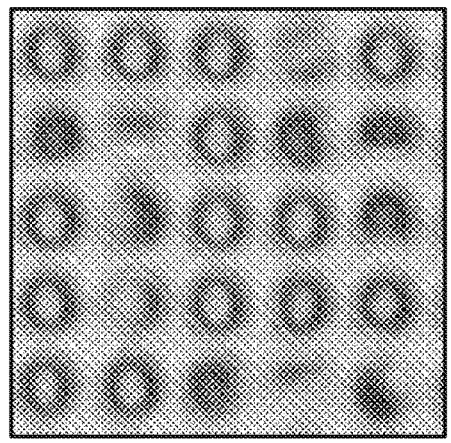
Fig. 9b
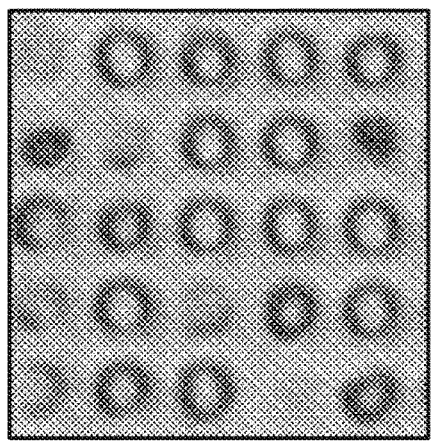
Fig. 9c
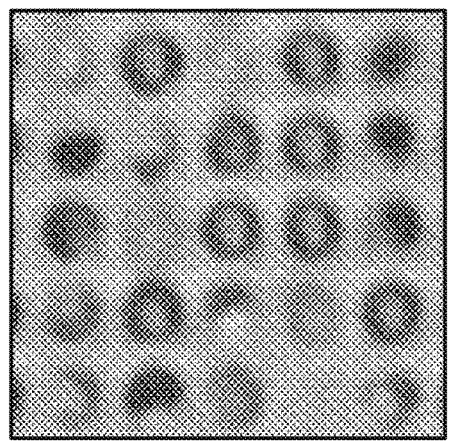
Fig. 9d
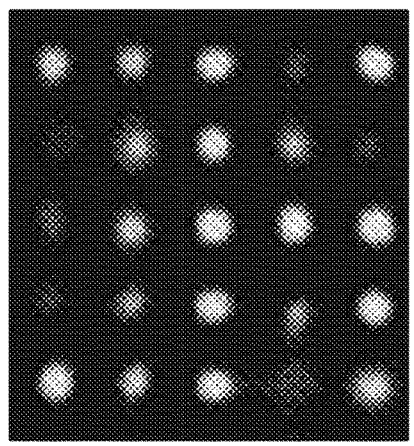
Fig. 9e
| 1  | 2  | 3  | 4  | 5  |
|----|----|----|----|----|
| 6  | 7  | 8  | 9  | 10 |
| 11 | 12 | 13 | 14 | 15 |
| 16 | 17 | 18 | 19 | 20 |
| 21 | 22 | 23 | 24 | 25 |
Fig. 9f

| row | column | | | | | | | |
|---|---|---|---|---|---|---|---|---|
| | 1 | 2 | 3 | 4 | 5 | 6 | 7 | 8 |
| 1 | A | A | A | K | K | K | A | A |
| 2 | - | K | A | K | A | K | A | A |
| 3 | K | A | K | A | A | K | K | K |
| 4 | K | A | A | K | A | A | K | K |
| 5 | K | K | K | A | K | A | K | K |
| 6 | A | K | A | K | A | K | A | A |
| 7 | A | A | K | K | K | K | K | K |
| 8 | A | K | K | K | K | K | K | A |

| row | column | | | | | | | |
|---|---|---|---|---|---|---|---|---|
| | 1 | 2 | 3 | 4 | 5 | 6 | 7 | 8 |
| 1 | Y | Y | Y | Y | D | D | Y | D |
| 2 | Y | D | D | D | D | Y | Y | Y |
| 3 | D | Y | Y | D | Y | D | D | Y |
| 4 | Y | Y | Y | D | D | Y | D | Y |
| 5 | D | Y | Y | D | Y | Y | Y | D |
| 6 | Y | D | Y | D | D | Y | D | D |
| 7 | D | Y | D | D | D | Y | Y | D |
| 8 | D | D | Y | Y | Y | Y | D | D |

| row | column | | | | | | | |
|---|---|---|---|---|---|---|---|---|
| | 1 | 2 | 3 | 4 | 5 | 6 | 7 | 8 |
| 1 | D | D | D | D | D | D | - | D |
| 2 | D | D | D | D | D | D | D | D |
| 3 | D | D | D | D | D | D | D | D |
| 4 | D | D | D | D | D | D | D | - |
| 5 | D | - | D | D | D | D | D | D |
| 6 | D | D | D | D | D | D | D | D |
| 7 | D | D | D | D | D | D | D | D |
| 8 | D | D | D | D | D | D | D | D |

| row | column | | | | | | | |
|---|---|---|---|---|---|---|---|---|
| | 1 | 2 | 3 | 4 | 5 | 6 | 7 | 8 |
| 1 | D | P | D | P | - | D | D | P |
| 2 | D | P | P | D | P | P | P | P |
| 3 | D | P | D | P | D | D | P | D |
| 4 | D | P | D | P | P | - | P | D |
| 5 | D | D | D | D | D | D | P | D |
| 6 | D | D | D | - | D | D | P | D |
| 7 | - | D | P | P | D | P | D | D |
| 8 | P | - | D | D | D | D | D | D |

| row | column | | | | | | | |
|---|---|---|---|---|---|---|---|---|
| | 1 | 2 | 3 | 4 | 5 | 6 | 7 | 8 |
| 1 | D | D | V | V | D | D | V | |
| 2 | V | - | V | V | D | D | V | V |
| 3 | D | V | - | - | V | V | - | V |
| 4 | - | D | D | V | V | D | V | D |
| 5 | D | D | V | D | - | V | V | - |
| 6 | D | D | V | V | V | V | D | V |
| 7 | D | D | V | - | V | D | D | D |
| 8 | V | V | - | V | V | V | D | D |

| row | column | | | | | | | |
|---|---|---|---|---|---|---|---|---|
| | 1 | 2 | 3 | 4 | 5 | 6 | 7 | 8 |
| 1 | D | K | K | D | D | D | D | K |
| 2 | D | K | K | D | D | D | D | K |
| 3 | D | K | K | D | D | D | D | D |
| 4 | D | D | D | K | K | K | - | K |
| 5 | K | D | K | D | K | D | D | D |
| 6 | K | D | K | D | K | K | K | D |
| 7 | D | D | K | D | K | K | D | - |
| 8 | D | K | D | K | D | K | K | D |

| row | column | | | | | | | |
|---|---|---|---|---|---|---|---|---|
| | 1 | 2 | 3 | 4 | 5 | 6 | 7 | 8 |
| 1 | Y | Y | Y | Y | Y | Y | Y | Y |
| 2 | Y | Y | Y | Y | Y | Y | Y | Y |
| 3 | - | Y | Y | Y | Y | Y | Y | Y |
| 4 | Y | Y | Y | - | - | Y | Y | Y |
| 5 | Y | Y | Y | - | Y | Y | Y | Y |
| 6 | Y | Y | Y | Y | Y | Y | Y | Y |
| 7 | Y | Y | Y | Y | - | Y | Y | Y |
| 8 | Y | Y | Y | Y | Y | Y | Y | Y |

| row | column | | | | | | | |
|---|---|---|---|---|---|---|---|---|
| | 1 | 2 | 3 | 4 | 5 | 6 | 7 | 8 |
| 1 | P | P | P | P | D | D | P | P |
| 2 | D | P | P | - | D | P | P | P |
| 3 | P | D | P | P | D | P | P | P |
| 4 | P | D | D | P | P | D | P | P |
| 5 | P | P | D | P | P | P | D | D |
| 6 | P | D | P | D | P | P | D | P |
| 7 | P | D | P | P | - | D | P | P |
| 8 | D | D | D | D | D | P | D | P |

| row | column | | | | | | | |
|---|---|---|---|---|---|---|---|---|
| | 1 | 2 | 3 | 4 | 5 | 6 | 7 | 8 |
| 1 | Y | Y | Y | Y | Y | Y | Y | Y |
| 2 | Y | Y | Y | Y | Y | Y | Y | Y |
| 3 | Y | Y | Y | Y | Y | Y | Y | Y |
| 4 | Y | Y | Y | Y | Y | Y | Y | Y |
| 5 | Y | Y | Y | Y | Y | Y | Y | Y |
| 6 | Y | Y | Y | Y | Y | Y | Y | Y |
| 7 | Y | Y | Y | Y | Y | Y | Y | Y |
| 8 | Y | Y | Y | Y | Y | Y | Y | Y |

SEQUENCE LISTING

```
<160> NUMBER OF SEQ ID NOS: 60

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 1

Ala Tyr Asp Asp Asp Asp Tyr Pro Tyr
1               5

<210> SEQ ID NO 2
<211> LENGTH: 9
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 2

Ala Tyr Asp Pro Asp Lys Tyr Pro Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 3

Ala Tyr Asp Asp Val Lys Tyr Pro Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 4

Lys Tyr Asp Pro Val Asp Tyr Pro Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 5

Lys Asp Asp Asp Asp Asp Tyr Asp Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 6

Ala Asp Asp Pro Val Lys Tyr Pro Tyr
1               5

<210> SEQ ID NO 7
<211> LENGTH: 4
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(4)

<400> SEQUENCE: 7

Lys Asp Asp Pro
1

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 8

Ala Asp Asp Pro Val Lys Tyr Pro Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(7)

<400> SEQUENCE: 9

Lys Asp Asp Asp Val Asp Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 10

Ala Asp Asp Pro Asp Asp Tyr Asp Tyr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 11

Lys Tyr Asp Pro Asp Asp Tyr Pro Tyr
1               5

<210> SEQ ID NO 12
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 12

Ala Tyr Asp Pro Val Asp Tyr Pro Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 13

Ala Tyr Asp Pro Val Lys Tyr Pro Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(6)

<400> SEQUENCE: 14

Lys Asp Asp Asp Asp Asp
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 15

Ala Tyr Asp Pro Val Lys Tyr Asp Tyr
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(4)

<400> SEQUENCE: 16

Lys Tyr Asp Asp
1
```

```
<210> SEQ ID NO 17
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(4)

<400> SEQUENCE: 17

Ala Asp Asp Pro
1

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 18

Ala Tyr Asp Asp Val Asp Tyr Asp Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 19

Lys Asp Asp Asp Val Asp Tyr Pro Tyr
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(4)

<400> SEQUENCE: 20

Lys Asp Asp Pro
1

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 21

Lys Tyr Asp Asp Val Asp Tyr Pro Tyr
1               5
```

```
<210> SEQ ID NO 22
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(4)

<400> SEQUENCE: 22

Lys Tyr Asp Asp
1

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 23

Ala Tyr Asp Pro Asp Asp Tyr Asp Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 24

Ala Tyr Asp Asp Asp Asp Tyr Asp Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(6)

<400> SEQUENCE: 25

Lys Asp Asp Pro Val Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(6)

<400> SEQUENCE: 26

Ala Asp Asp Pro Val Lys
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(5)

<400> SEQUENCE: 27

Lys Asp Asp Pro Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 28

Lys Asp Asp Asp Asp Lys Tyr Pro Tyr
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 29

Lys Tyr Asp Asp Val Lys Tyr Asp Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(6)

<400> SEQUENCE: 30

Ala Asp Asp Asp Asp Asp
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(4)

<400> SEQUENCE: 31

Lys Tyr Asp Asp
```

```
<210> SEQ ID NO 32
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 32

Ala Tyr Asp Asp Val Asp Tyr Pro Tyr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 33

Lys Tyr Asp Pro Val Asp Tyr Asp Tyr
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(4)

<400> SEQUENCE: 34

Lys Asp Asp Asp
1

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 35

Ala Tyr Asp Asp Asp Lys Tyr Pro Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 36
```

```
Lys Asp Asp Asp Asp Tyr Asp Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 37

Ala Tyr Asp Asp Val Lys Tyr Pro Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 38

Ala Asp Asp Asp Val Asp Tyr Pro Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Peptide from table 3
<220> FEATURE:
<221> NAME/KEY: peptide
<222> LOCATION: (1)..(9)

<400> SEQUENCE: 39

Lys Tyr Asp Asp Val Lys Tyr Pro Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 40

Ala Asp Asp Pro Asp Lys Tyr Asp Tyr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 41
```

```
Ala Asp Asp Asp Val Asp Tyr Pro Tyr
1               5
```

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 42

```
Ala Tyr Asp Asp Asp Asp Tyr Asp Tyr
1               5
```

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(9)

<400> SEQUENCE: 43

```
Lys Asp Asp Pro Val Lys Tyr Pro Tyr
1               5
```

<210> SEQ ID NO 44
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(4)

<400> SEQUENCE: 44

```
Lys Asp Asp Pro
1
```

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(6)

<400> SEQUENCE: 45

```
Lys Asp Asp Asp Val Lys
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

```
<400> SEQUENCE: 46

Lys Tyr Asp Pro Asp Lys Tyr Asp Tyr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 47

Lys Tyr Asp Asp Asp Asp Tyr Pro Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(5)

<400> SEQUENCE: 48

Lys Tyr Asp Asp Asp
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 49

Ala Asp Asp Pro Val Asp Tyr Asp Tyr
1               5

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(4)

<400> SEQUENCE: 50

Lys Tyr Asp Asp
1

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)
```

```
<400> SEQUENCE: 51

Lys Tyr Asp Asp Val Lys Tyr Asp Tyr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 52

Lys Tyr Asp Asp Val Asp Tyr Asp Tyr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 53

Lys Tyr Asp Asp Val Lys Tyr Pro Tyr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(9)

<400> SEQUENCE: 54

Lys Asp Asp Asp Asp Lys Tyr Asp Tyr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(9)

<400> SEQUENCE: 55

Ala Asp Asp Asp Asp Asp Tyr Pro Tyr
1               5

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
```

```
<222> LOCATION: (1)..(15)
<220> FEATURE:
<221> NAME/KEY: MISC_FEATURE
<222> LOCATION: (1)..(4)
<223> OTHER INFORMATION: Xaa = any amino acid
<220> FEATURE:
<221> NAME/KEY: MISC_FEATURE
<222> LOCATION: (9)..(10)
<223> OTHER INFORMATION: Xaa = any amino acid
<220> FEATURE:
<221> NAME/KEY: MISC_FEATURE
<222> LOCATION: (12)..(15)
<223> OTHER INFORMATION: Xaa = any amino acid

<400> SEQUENCE: 56

Xaa Xaa Xaa Xaa Asp Tyr Lys Asp Xaa Xaa Asp Xaa Xaa Xaa Xaa
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: peptide
<222> LOCATION: (1)..(15)
<220> FEATURE:
<221> NAME/KEY: MISC_FEATURE
<222> LOCATION: (1)..(4)
<223> OTHER INFORMATION: Xaa = any amino acid
<220> FEATURE:
<221> NAME/KEY: MISC_FEATURE
<222> LOCATION: (9)..(10)
<223> OTHER INFORMATION: Xaa = any amino acid
<220> FEATURE:
<221> NAME/KEY: MISC_FEATURE
<222> LOCATION: (12)..(15)
<223> OTHER INFORMATION: Xaa = any amino acid

<400> SEQUENCE: 57

Xaa Xaa Xaa Xaa Asp Tyr Lys Glu Xaa Xaa Asp Xaa Xaa Xaa Xaa
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(7)

<400> SEQUENCE: 58

Lys Asp Asp Asp Lys Tyr Asp
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(8)
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
```

```
<222> LOCATION: (5)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid

<400> SEQUENCE: 59

Xaa Lys Tyr Asp Xaa Xaa Lys Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: Peptide
<222> LOCATION: (1)..(8)
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid

<400> SEQUENCE: 60

Xaa Lys Tyr Asp Xaa Xaa Asp Xaa
1               5
```

ULTRA HIGH-DENSITY OLIGOMER ARRAYS AND METHOD OF PRODUCTION THEREOF

CROSS REFERENCES TO RELATED APPLICATIONS

This application is a continuation of international patent application PCT/EP2016/074542, filed on Oct. 13, 2016 designating the U.S., which international patent application has been published in German language and claims priority from German patent application 10 2015 117 567.3, filed on Oct. 15, 2015. The entire contents of these priority applications are incorporated herein by reference.

INCORPORATION OF ELECTRONIC SEQUENCE LISTING

The Sequence Listing is submitted as an ASCII text file, created on Apr. 23, 2018, 14.5 KB, which is incorporated by reference herein.

BACKGROUND OF THE INVENTION

The present invention relates an oligomer array and a method of producing an oligomer array, such as for instance a peptide array. In addition also the use of such an oligomer arrays for detecting a binding partner is described.

Oligomer arrays are well-known within the prior art and refer to the entirety of the oligomers that are combinatorially synthetized onto a carrier or a substrate, respectively (consisting of individual molecular components, such as e.g. monomers). Herein they bind covalently on a carrier being configured as spots. The synthesis of these oligomers in general resides on the chemical principles of the solid-phase synthesis. The realization of the parallel solid-phase synthesis, in particular the transport of the monomers to the respective synthesis location, herein is of decisive importance.

Such oligomers immobilized on an oligomer array comprise all kinds of oligomers that can be synthetized combinatorially from several components. Examples of such components comprise amino acid derivatives and nucleotide derivatives, such as deoxyribonucleotide derivatives and ribonucleotide derivatives.

The oligomer arrays mentioned above are of interest in particular with respect to the detection/determination of binding partners. Herein for instance a suitable binding partner is determined by means of hybridization. The existence of a respective binding event for instance may establish the inhibition of the effect of a biomolecule, whereby the utilization of the respective inhibiting oligomer as a medicament is made possible. The parallel search of as many oligomers as possible being potentially biological active therefore is of high importance within medicine and adjacent branches. To make possible a parallel searching of a large number of oligomers, in particular the preparation of ultra high dense oligomer arrays is of interest within which more than $10^6$ oligomers per square centimeter or spots/cm$^2$, respectively are present on the carrier immobilized.

Within the prior art there is known a variety of different methods for producing oligomer arrays. These methods for preparation of polynucleotides in particular are characterized by a simplified production, when compared to the peptide synthesis, this being the case since substantially only four components are utilized. For instance the synthesis of a library of oligonucleotide sequences can be initially performed by means of an oligonucleotide synthesizer that is highly parallel including an intermediate PCR increase. The finally synthesized strands subsequently are coupled into microparticles (beads) so that per microparticle there is a kind of an oligonucleotide sequence. Thereafter the microparticles are arranged on a surface within array format, and the location of the microparticles and thee sequences of the respective oligonucleotides are determined using a special hybridization technique. However, this method is limited to oligonucleotides (Gunderson K. L. et al.; Genome Research; 14(5) (2004), pp. 870-877).

Further methods for generating oligonucleotides comprise phage display and ribosomal display methods. Herein synthetically generated oligonucleotides are fused with the gene of a phage shell protein so that after transfection of a bacterium each bacterium "packs" a different kind of phage that only differs within the sequence of the peptides fused with the phage shell protein (cf. Smith, G. P. filamentous fusion phage—novel expression vectors that display cloned antigens on the virion surface; Science 228 (1985) pp. 1315-1317).

The combinatorial peptide synthesis using semiconductor chips for instance may be a high voltage CMOS chip the surface of which is divided into different electrodes (M. Beyer et al., Science, 318 (5858), 1888, 2007). By programming the chip individual electrodes can be activated selectively. By means of the electric fields generated thereby loaded particles that serve as carriers for the monomers are deposited at the electrodes thereof at precise locations. The synthesis of the oligomer arrays may either be performed directly on the chip surface or on a target carrier (for instance a glass object slider). To this end particle patterns generated on the CMOS chip are transferred onto the target carrier by means of an electric field.

In addition lithographic methods are known by means of which spot densities of up to $10^6$ spots/cm$^2$ can be obtained (Fodor S. P. A. et al.; light-directed, spatially addressable parallel chemical synthesis. Science 251, pp. 767-773 (1991); and Legutki J.-B. Nat. Commun. 5, 4785, 2014). Using light masks protective groups are separated according to the generated light pattern that allows the binding of a subsequent amino acid parts. Apart from the necessity of a precise positioning of the synthesis carriers such a lithographic method has a further disadvantage that for each monomer there must be performed a separate coupling reaction. This inevitably leads to secondary reactions that prevent that peptide arrays of sufficiently good quality are commercially available (Palloys J. P. et al.; individually addressable parallel peptide synthesis on microchips; Nature Biotechnology 20 (2002), pp. 922-926).

In the case of the combinatorial laser fusing (CLF) monomer-containing particles are fixed directly on a synthesis carrier by means of laser irradiation. Herein a laser beam is guided across the carrier to selectively melt the particles (Maerkle F. et al., High-Density Peptide Arrays with Combinatorial Laser Fusing, Advanced Materials, Volume 26 (2014), pp. 3730-3734).

A further method relates to a xerographic method wherein the toner particles of a 24 color laser printer are printed that each contain an amino acid component for the combinatorial synthesis. Such a method is for instance described in WO 00/35940.

The lithographic method described above needs a variety of coupling cycles, if an oligomer array and, in particular a peptide array, shall be generated thereby. The number of coupling cycles can be computed from N×Y, wherein N refers to the number of the different monomers and Y refers to the length of the oligomers. If for instance an array of 15 mer peptides shall be synthesized within which 20 amino acids are used, than the number of coupling cycles is computed to be 300. Due to this reason lithographic methods up to now only are used successfully for the synthesis oligonucleotide arrays. Therefore currently there is no other commercially available method by means of which spot densities of more than 40,000 spots/cm$^2$ can be realized with sufficiently high quality. A further technical problem are the complicated and costly devices that are necessary for the lithographic and also for all other methods.

SUMMARY OF THE INVENTION

In view of this it is a first aspect of the present invention to disclose a method by means of which oligomer arrays can be generated using only few coupling steps. A further aspect is the disclosure of a method by means of which high density and ultra high-density oligomer arrays can be provided in a simple way. A further aspect is the disclosure of a method by means of which devices are used having a simple and cost-effective design. A further aspect is the disclosure of a method which allows for a fast generation of oligomer arrays in that for instance the exact positioning of the substrate is no longer necessary. A further aspect is the disclosure of respective oligomer arrays and the utilization thereof for determining suitable binding partners.

According to one aspect the invention discloses a method of producing oligomer arrays comprising the following steps:
  a) providing a substrate having a plurality of recesses;
  b) placing a first particle with a first molecule into a recess;
  c) releasing the first molecule from the first particle;
  d) binding the first molecule to a second molecule while forming an oligomer, wherein the second molecule is immobilized within the recess;
  e) optionally repeating steps (b) to (d) while elongating the oligomer;
  wherein at least a first particle and/or a first molecule comprises a detectable marker.

According to a further aspect of the present invention an oligomer array is disclosed that can be obtained according to the above-mentioned method.

According to a further aspect of the present invention an oligomer array is disclosed, comprising:
  a plurality of recesses;
  a plurality of oligomers that are located within the recesses, wherein an oligomer comprises at least a first molecule and a second molecule,
  wherein the second molecule is immobilized within a recess, wherein a part of the several oligomers comprises a plurality of identical first molecules at a specific oligomer position.

According to a further aspect of the present invention the utilization of an oligomer array for determining a binding partner is disclosed.

According to a further aspect of the present invention there is disclosed a particle having a molecule that is arranged therein, or is embedded therein, respectively. The molecule to this end is adapted for binding to a further molecule within the frame of a solid-phase synthesis and/or to a substrate functionality. The particle and/or the molecule in addition comprise a detectable marker.

The present invention is based on a waiver of a controlled transport of the monomers or molecules, respectively, to the synthesis locations. Instead the transport of the monomers to the synthesis locations occurs stochastically or randomly, respectively, that means it cannot be determined in advance, which monomer will be fixed at which location. After the binding of the individual monomers only the final position is registered. Thereby after the completion of the array in retrospect there can be generated a 3D deposition mask that contains all necessary information with respect to the location and the structure of the oligomers of each spot. By dispensing with the controlled deposition of the molecules thereby the simple and most cost-effective production of ultra high-dense oligomer arrays, and in particular peptide arrays, with spot densities of up to 1,000,000 spots/cm$^2$ and even more is made possible, since present particle mixtures that are placed into the recesses of a substrate, such as a microstructured glass carrier, can be detected and subsequently be processed in parallel for freeing and binding the monomers, e.g. by heating.

By utilizing the particle based transfer of the molecules into a recess there can be obtained (i) a simplified transfer of molecules into a recess of the substrate, e.g. by depositing or rubbing a solution containing the particles into the recesses. In addition (ii) only one oligomer can be immobilized within a recess from (one) particle. By using a particle shape that is adapted to the shape of the recess, i.e. usually the particle and the recess have fitting cross sections, it can be ensured that (iii) an oligomer (of a particle having a particular cross section) is immobilized within a specific recess having a fitting cross section. The number and kind of the particles per recess herein can be controlled by means of the cross section/shape of the recess and the cross section/shape of the particle. Preferably the particle dimensions and the cross section of the recess are selected so that a single particle fits within one recess. More preferably the cross section of the recess is substantially circular and the cross section of the particle is substantially circular with so small dimensions that a single particle fits into a recess. The depth of the recess is selected herein so that only a single particle fits into a recess. The present approach in addition (iv) allows to occupy or block, respectively, particular recesses by introducing particles into such recesses that are not depleted within the frame of the oligomer synthesis. That means for instance particles of a different chemical composition than the particle are utilized for placing a component, e.g. a monomer, into a recess.

According to the method according to the invention at least one of the first particles and/or the first molecules comprises a detectable marker. The detectable marker may e.g. be a fluorescent or luminescent marker. Alternatively the marker may be a polynucleotide the determination of which is done by hybridization. With a plurality of different (first) molecules which within a synthesis step shall be coupled stochastically by selecting a suitable detectable marker the characterization of the oligomers that are respectively elongated by a position can be performed. The number of different oligomers which for each coupling step are binded herein is not limited, but only requires a respective marking of the first molecule and/or the first particle. It should also be clear that the number of markings with the number of placed first particles per reaction step not necessarily conforms with a first molecule, that instead by combining different markings also mixed colors can be generated that allow to determine or assign, respectively, the first molecule with the respective recess without any doubt.

With the method according to the invention after one of the steps b), c) or d) the determination of the detectable marker can be performed. After step b) herein preferably the detectable marker is determined which is present on the particle surface. After steps c) and/or d) the determination of detectable markers that are bound covalently to the first molecule is performed.

Preferably the method of providing an oligomer array comprises the following steps: a) providing a substrate comprising a plurality of recesses; b) placing a first particle with a first molecule stochastically into a recess; c) releasing the first molecule from the first particle; d) binding the first molecule to a second molecule while forming an oligomer, wherein the second molecule is immobilized within the recess; e) optionally repeating steps (b) to (d) while elongating the oligomer; wherein at least a first particle and/or a first molecule comprises a detectable marker. Preferably several first particles are utilized, wherein each of the several first particles respectively comprises identical first molecules, and each of the several first particles comprises a detectable marker, which is different from the marker of a different of the several first particles.

Preferably the generally known principles of the solid phase synthesis, e.g. the synthesis of polynucleotides, polypeptides and other polymers are used. The performing of such solid-phase syntheses, including the reagents, reaction conditions and the protective group chemistry etc. are known to the skilled person and can be easily applied to the present method. In this way it is made possible to provide oligomer arrays for a plurality of different oligomer components, or molecules, respectively. It is obvious that oligomer arrays may consist of components different from nucleotides, or nucleotide derivatives, respectively, or peptides or peptide derivatives, respectively. Polymers may also comprise different components, such as nucleotide derivatives and amino acid derivatives. The nucleotide derivatives and amino acid derivatives herein may be of natural or artificial origin. Basically an oligomer may comprise a sequence of any kind of molecules.

As used herein the term "array" refers to the two-dimensional arrangement of a plurality of oligomers within the recesses of a substrate. Preferably these are highly dense oligomer arrays having a density of $10^3$ spots/cm$^2$ or more, preferably $10^4$ spots/cm$^2$ or more, respective $10^5$ spots/cm$^2$ or more. Preferably these are ultra high-density oligomer arrays with a density of $10^6$ spots/cm$^2$ or more, $2.5\times10^7$ spots/cm$^2$ or more, $5\times10^7$ spots/cm$^2$ or more, or $7\times10^7$ spots/cm$^2$ or more, respectively.

The term "oligomer" as used herein relates to the (maximum) chain length of a chemical compound comprising a plurality of molecules. The molecules herein may be the same or may be different. Preferably uniform molecules, such as e.g. amino acids or amino acid derivatives, respectively, or nucleic acids or nucleic acid derivatives are utilized. Thus an oligomer is characterized by the maximum chain length thereof, which usually comprises 2 to 30 molecule units. Preferably an oligomer comprises 2 to 25 molecule units, 3 to 20 molecule units, 4 to 19 molecule units, 5 to 18 molecule units, 6 to 17 molecule units, 8 to 16 molecule units, 9 to 15 molecule units, 10 to 14 molecule units, 11 to 13 molecule units or 12 molecule units. More preferred are 5 to 18 molecule units, 8 to 15 molecule units and 12 to 15 molecule units. The term maximum chain length herein designates the backbone of the oligomer, wherein one end thereof can be immobilized at the substrate directly or by means of a spacer, and the other end thereof can be provided with a further first molecule. Oligomers also may comprise branchings and/or ring closures, wherein side-chain functionalities of the individual molecules/monomers can be obtained using a suitable reaction partner.

The term "substrate" as used herein refers to a carrier of an oligomer array and comprises materials such as glass, quartz, silicon, ceramics, plastics, metals and/or composite materials. Preferably substrates are made of quartz glass, e.g. object sliders made of quartz glass.

The terms "diameter" and "dimension" as used herein relate to the diameter or the dimension of a particle or a recess and usually are within a range of a few µm, such as 0.1 to 100 µm. The diameter, or the dimensions respectively, of a particle or of the recess are determined by the production method. E.g. the structuring of a surface of a substrate can be performed using a laser with the desired precision. However, the skilled person is well aware that with the present invention not the precision of the "diameter" or the "dimension" is decisive, but instead the fitting of a particle into a recess, preferably of a single particle into a single recess. Herein usually only the size relations and the dimensional relations are decisive. Thus for instance particles may be produced that only approximately have a diameter fitting to a recess, since larger particles can be usually removed, e.g. washed away. In addition the occupation of a recess with a particle, preferably of a single recess with a single particle, can be verified by using a detectable marker. E.g. it can be determined in this way, whether preferably a single particle is present within a single recess, or whether possibly two or more particles are present within a single recess. For instance the presence of two particles with identical detectable (fluorescent) markers within a single recess can be determined when compared to the presence of a particle with a respective marker within a single recess by the different (fluorescent) intensities. If for instance two particles with different detectable (fluorescent) markers are present within a single recess, then the respective markers, e.g. by means of different absorption maxima within the fluorescent spectrum, make possible the distinct detection of the particle. The diameter preferably is the median diameter.

The median diameter in the case of a particle may e.g. be determined by means of a Coulter counter according to ISO 13319:2007. Within the scope of the present application a Beckman Coulter Multisizer 3 was used. All measurements were performed as specified by the manufacturer.

The dimensions of the substrate can be determined by means of white light interferometry according to EN ISO 25178. Within the scope of the present invention a Bruker VSI Contour K0 was used. All measurements were performed as specified by the manufacturer. Suitable substrates can e.g. be purchased from AMO GmbH, Aachen, Germany.

The term "recess" as used herein relates to a recess or a depression or a valley within the surface of a substrate. The recesses herein are arranged two-dimensionally and are at such a distance from each other that there is no overlap and thus single recesses are present that are distinct from each other. The number of recesses herein reflects the density of the array. The cross section of the recesses and the depth thereof allows to receive one or more particles. Preferably only one particle fits into one recess. A control of the particles per recess herein can be performed by selecting a suitable cross section of the recess that is adapted to the cross section of the particle. For instance a recess and a first particle each have a substantially circular or a polygonal cross section, such as for instance a pentagonal, a quadrangular or a triangular cross section. Substantially circular or substantially polygonal respectively means that the ratio of the maximum length of the recess to maximum width of the recess is between 1.0 and 1.2, preferably 1.0 to 1.15, 1.0 to 1.1, 1.0 to 1.05 and 1.0 to 1.01. Preferably, the recess is ideally circular or ideally polygonal, respectively. The depth of the recess is preferably selected so that a single particle fits into one recess. The aspect ratio e.g. is 0.5 to 1.5, preferably 0.6 to 1.4, 0.7 to 1.3, 0.8 to 1.2, 0.9 to 1.1, and am mostly preferred 1. Exemplary diameters of a recess comprise 0.1 to 100 µm, preferably 0.8 to 50 µm, 1 to 15 µm, 2.5 to 14 µm, 5 to 13 µm, 6 to 12 µm, 7 to 11 µm or 8 to 10 µm, such as for instance 9 µm. The distance from center to center (pitch) of the individual recesses with respect to each other is selected so that the recesses are present individually on the substrate, and a part from there is no further limitation. The pitch may for instance be from 1 to 70 µm, preferably 10 to 40 µm, 20 to 30 µm or 25 µm.

The production of an oligomer array, such as a peptide array according to the invention comprises substantially a sequence of the following steps:

Particles containing molecules for the combinatorial synthesis are filled into the recesses/microcavities of the substrate by coincidence, wherein preferably a mixture of different molecule particles is used, such as twenty different kinds of particles which each comprise one of twenty different oligomers, or oligomer derivatives, respectively, such as amino acids or amino acid derivatives, that are suitable for the solid-phase synthesis. Herein the particle size is selected so that into each recess there fits only one particle. Within one molecule particle there may be present several different molecules, such as 2 or more molecules different from each other, 3 or more molecules different from each other, 4 or more molecules different from each other, 5 or more molecules different from each other, or 10 or more molecules different from each other. Preferably within one particle there are molecules which are not different from each other, i.e. a specific molecule type. Herein a respective marking of the particles and/or molecules should be looked after to allow a unique identification of the molecules. Preferably the molecules are present within the inside of a particle, i.e. not bound covalently to the particle.

Preferably the molecule particles are monomer particles within which there is only a specific molecule within/at a particle. Thereby it is ensured that only a specific monomer immobilizes within a recess. Preferably the molecule is contained within the inside of the particle, i.e. not bound covalently to the particle.

For instance particles of a styrene-acrylate copolymer are used as a matrix having a median diameter of 3 µm per particle. Further suitable particles, the synthesis thereof, as well as the synthesis with monomers contained therein may for instance be taken from WO 2014/169928 and DE 101 56 329 A1 the contents of which are fully incorporated herein by reference. The first molecule for instance is present within a first particle, so that the first particle fully surrounds the first molecule. Alternatively the first molecule may also be attached to the surface of the first particle, for instance bound covalently thereon.

In the next step the first molecule is released from the first particle, or out of the first particle, respectively. When using styrene-acrylate copolymers as a matrix material for the first particle, this may be done by increasing temperature. For instance the oligomer array with a (plurality) of first particles with different first molecules is placed within a plurality of recesses so that within each recess there is one first particle. By heating to 80° C. or more, such as 80° C. to 120° C., 85° C. to 110° C. or 90° C. to 100° C., the release of the first molecule from the first particle occurs. The temperature increase may also facilitate the binding of the first molecule to the second molecule, such as in the case of the synthesis of a peptide array. The release of the first molecule from the first particle and possibly the binding of the first molecule to the second molecule may for instance occur within a time span of 30 minutes to 2 hours, preferably 1 to 2 hours, such as 90 minutes. The reaction possibly occurs under exclusion from air oxygen, such as under argon atmosphere or under atmosphere of a different inert gas, such as a different noble gas or nitrogen so that a reaction of air oxygen with the first molecule and/or the second molecule, or the oligomer, respectively, is substantially avoided. Preferably herein an undesired oxidation of the reactants or the reaction partners, respectively, is substantially excluded. The production of the particles, or the binding of the molecules contained therein, respectively, as well as the basic conditions, reagents, used devices, etc. can be taken from WO 00/35940 the contents of which are fully incorporated herein by reference.

Preferably the release of the first molecule from the first particle, or out of the first particle respectively, and/or the binding of the first molecule within the presence of a solvent occurs within a vapor phase. To this end the substrate is exposed to an unsaturated and/or a saturated vapor atmosphere of the solvent. The vapor condenses on the surface of the substrate and/or is absorbed by the first particle. Thereby the polymer matrix becomes permeable, i.e. perforated and/or dissolved, and the first molecule contained therein is released. By contrast to the sole release by temperature increase thereby on the one hand considerable larger amounts of molecules can be released and on the other hand these released molecules can more simply diffuse to the reactive groups on the substrate. The solvent preferably is configured as one or more organic solvents. For generating the vapor atmosphere for instance dichloromethane, acetone, N,N-dimethylformamide and/or combinations thereof can be utilized as organic solvents. The extraction of the molecules can be performed at temperatures between −20° C. and +110° C., preferably 10 to 80° C., 60 to 80° C. Higher temperatures of for instance >80° C. to 110° C. usually simplify the extraction and binding of the molecules. Lower temperatures of for instance −20° C. to <10° C. impede the diffusion of the molecules during extraction. The extraction usually takes between 1 minute and 90 minutes. The duration herein usually depends on the used solvent and on the temperature and can easily be determined by the skilled person.

The second molecule may e.g. have a coupling functionality within a recess of the substrate, such as an amino group directly applied to the substrate surface. Thereafter the first molecule can bind to the surface functionality. Alternatively it may be a spacer immobilized within a recess, or a spacer, respectively, with an attached coupling functionality. In addition the second molecule may be a single molecule or may consist of several molecules of the oligomer array. The step of binding the first molecule to the second molecule thus refers either to the attachment of the first oligomer molecule to the substrate, directly thereto, or indirectly by means of a spacer or any extension, or elongation step, respectively, of the oligomer, such as from 2 mer to a 3 mer, 10 mer to a 11 mer, or also from a 12 mer to a 15 mer, in case the first molecule may already comprise several (three) oligomer molecules.

Before building the oligomer array according to the invention, the surface functionality may be modified so that the physiochemical characteristics of the lands between the recesses and the recesses themselves vary. The surface of the lands between the cavities may be modified so that it impedes the diffusion and thereby the binding of the first molecule from a cavity to the adjacent cavities.

For instance this modification of the surface between the lands can be done by etching the surface of the lands, whereby the recesses themselves are not exposed to the etching medium. On the one hand the recesses may be protected against the etching medium by a polymer matrix that is placed within the cavities before the etching process and sintered for a homogenous filling. Alternatively the surface within the recesses can be protected against the etching medium by a sputtered metal layer. To this end the total substrate is covered with a metal layer which subsequently is removed from the surface of the lands. The etching for instance can be performed by means of a cleaning plasma (oxygen, nitrogen or argon plasma or different gas plasmas), or by means of a liquid medium of a strong acid or a strong base. The single requirement is that the material protecting the cavities is chemically inert against the etching medium that is used.

When the etching of the surface of the lands is completed, then the material protecting the recesses is removed from the recesses. The possibly used polymer matrix may herein for instance be removed by organic solvents. A metal layer can be removed by anorganic solvents.

After the etching of the surface of the lands between the cavities has been performed, then the surface of the lands can be chemically modified. For instance hydrophobic silanes may be coupled to OH-groups generated during the etching process. Thereby the diffusion of the molecules between the individual cavities during extraction can be impeded.

Apart from the possibility of the etching there is a possibility to modify the surface of the lands by activating photosensitive groups. To this end the surface functionality of the total substrate is coupled to a photosensitive linker which can be separated by irradiating with UV light. This irradiation can for instance be done by means of a so-called mask aligner, as known in semiconductor manufacture. After the separating of the linker the surface on the lands between the cavities can be made hydrophobic, whereby the diffusion of the molecules between the individual recesses during the later occurring extraction is impeded. After making hydrophobic the photosensitive linker within the cavities is separated. Thereafter step (b) the placing of a first particle with a first molecule within a recess can be performed and additional steps can be performed.

During the step of the release of the first molecule from the first particle and/or during the step of the binding of the first molecule to the second molecule the recesses may be sealed while forming an oligomer. This impedes the diffusion of the first molecule, or of the first molecules, respectively, out of the recesses and a contamination of different recesses occurring therewith, or respectively, ensures a lower rate. The sealing may for instance be performed by applying a sealing material onto the substrate surface. The sealing can be ensured by the contact of the sealing material and the substrate surface. Thus each cavity is a closed system within which the release and/or the binding of the molecule, or the molecules respectively, occur fully independently from the other cavities of the substrate. As a sealing material for instance PDMS, PTFE, PFDV membranes or other commercially bonding strips can be used. Alternatively or in addition each other method step, within which an isolation from the environment is desired, can be performed accordingly, i.e. by sealing the recess.

After the placing step for each plane of the synthesis the location of the different monomer particles is determined. This may be performed preferably in that the particles are coded before with fluorescent colorants or with luminescent colorants, respectively, so that a CMOS sensor, a CCD camera or a fluorescence scanner can be utilized for detecting within which cavity there is located which particle. The coding of the different first molecules and/or of the first particles can be performed by the different fluorescent colorants, or luminescent colorants, respectively by using different concentrations thereof, and by combining possibly colorants of different concentrations. In this way for instance three different colorants in two different concentrations may code six different particles or, if these can still be combined with each other, then 6×6=36 different particles can be coded.

The utilization of the first particle with a first molecule (each) allows the production of arrays with ultra high spot densities, such as 106 spots/cm$^2$ or more. The first particles may be placed within respective recesses by simple brushing techniques so that a distinct placing of the first particles is not necessary according to the method of the invention. Thereby the method according to the invention is different from the methods according to the prior art, since these require a distinct placing of the particles.

The synthesis method in analogy to the solid-phase synthesis may comprise the simplified integration of oligomers, or modified oligomers, respectively, and reactions thereof without elongation of the oligomers. For instance within amino acids functionalities, i.e. reactive groups, can be specifically reacted so that at this location that does not correspond to the backbone of the oligomer, e.g. one or more further molecules can be built in or a cyclization within the oligomer occurs. It is clear that a respective protective group chemistry must be used to allow the particular reaction of the molecules and to avoid undesired reactions. Within the prior art a plurality of protective groups is known which can be placed selectively and can be removed thereafter.

The detectable marker can be visualized by a suitable method, e.g. for generating a 3D deposition mask of the oligomer array. In addition also image forming methods can be utilized that comprise any kind of device or apparatus within which an image signal or an image can be generated in reaction to a detection of a detectable marker. The device allows for a two-dimensional localization of the detectable marker on the substrate and thus for a distinct detection of the molecule with respect to its position within the oligomer and the recess within the substrate.

"Spacers" or "linkers", such as utilized for instance with the oligomer array according to the invention or the method respectively for the production thereof, are characterized in that they comprise a first end that within the recess of the substrate is bound to the substrate surface, and a second end, that is bound to the oligomer, or to an oligomer molecule, respectively. The spacer thus divides the substrate from the oligomer, or the oligomer molecule, respectively, however is linked with both. Herein the spacer at the end is bound covalently to the substrate and to the oligomer, or the oligomer molecule, respectively.

Spacers can be directly synthesized as a substrate surface, this followed by a generation of a covalent binding to the first molecule, or in total with the substrate, and can be subsequently connected with the first molecule. Bindings within the spacer may comprise C—C single bindings, C—C double bindings, C—N single bindings or C—O single bindings. In addition the spacer may comprise side chains or other substituents. The substrate and the first molecule can be connected to the spacer by means of a suitable reaction, to generate in this way a covalent binding therebetween. Suitable spacers comprise alkyl, alkynyl, alkynyl chains, aromatic, polyaromatic and heteroaromatic rings, wherein each of which can further be substituted. Spacers preferably have a linear C—C base body of a length of 10 to 25 carbon atoms, preferably 12 to 18 carbon atoms, such as about 15 carbon atoms. Alternatively, the oligomer components can be used as spacers. For instance a 15 mer polyglycine can be used as a spacer for a peptide array. It will be understood that the length of the spacers and the characteristics thereof can be freely chosen, as necessary. Suitable spacers, the production thereof and the reaction thereof with the substrate and/or with a molecule of an oligomer to be prepared are well known to the skilled person.

The spacers can be selected so that a good access of a binding partner to the oligomer is made possible and/or that the oligomer is free to move at the substrate surface. In addition the spacer may be designed so that a chemical decomposition at or within the spacer is made possible to allow thereby a selective separation of a particular oligomer. This has the advantage that the oligomer can be examined without any interference by the substrate.

There is a possibility to also include spacers that can be separated within the synthesis of the oligomer arrays. Thereby synthesized oligomers can be easily separated and transferred onto a target surface. In addition this allows a cleaning of the oligomers, since only fully synthesized oligomers are transferred. The residual products (not fully synthesized oligomers) on the other hand are not transferred and can be removed during a washing step. Complete oligomers are those oligomers that have a chain length corresponding to the number of passed steps according to the present methods, i.e. the number of monomers of the oligomer to be obtained. In addition the oligomer arrays can be multiplied by the transfer. By controlling the separating rate in percent thus several replicates of the same oligomer arrays can be obtained.

The separating of the molecules is obtained by the incorporation of spacers that can be separated at the basis of the oligomers. The skilled person is aware of stable spacers that can be separated for instance by light, in particular by UV light or hydrogenolysis or photolysis under basic conditions etc. that are stable against the reaction conditions of a synthesis. Selectively fissible linkers that may be based on a methionine and an ester group can for instance be taken from DE 69435011 T2. Fields G B and R L Noble, 1990, Solid phase peptide synthesis utilizing 9-fluorenylmethoxycarbonyl amino acids, Int. J. Pept. Protein Res. 35: 161-214 discloses further linkers of this kind. Examples of further spacers are the Rink amide linker or the UV-fissible linker which can be taken from M. S. Bernatowicz, S. B. Daniels, H. Köster, Tetrahedron Lett. 30 (1989) 4645 or Stefan Peukert and Bernd Giese, The Pivaloylglycol Anchor Group: A New Platform for a Photolabile linker in Solid-Phase Synthesis, J. Org. Chem. 1998, 63, 9045-9051.

For the transfer the cavities are filled with a buffering solution. The composition of the buffer depends on the characteristics of the synthesized oligomers and is known to the skilled person. To impede during transfer the diffusion of the oligomer from one cavity into adjacent cavities, for instance a membrane may be used as the target surface which seals the individual cavities. After the placing of the membrane the separation of the spacer is performed. All oligomers (totally synthesized oligomers as well as residual products) can now move freely within the cavities filled within the buffering solution within the limits of the diffusion.

To now transfer the totally synthesized oligomers and thereby effect a cleaning of the oligomer arrays, in the last step of the oligomer synthesis a functional group was coupled to the end groups of the oligomers. This may for instance according to the solid-phase synthesis of Merrifield only couple to the completely synthesized oligomers, since the residual products are already acetylated (blocked). These functional groups may enter a binding with the target surface that is also functionalized. Examples of such bindings are biotin-streptavidin, azide-alkyne or thiol-gold interactions. After the fission of the synthesis products only completely synthesized oligomers will bind with the functionalized target surface, while the residual products are washed away.

When compared to the methods known in the prior art so-called "focused" oligomers or oligomer libraries can be more easily synthesized. For instance at any coupling levels there can be processed, such as for instance a coupling level 5, 8, 9, 10, 11, computed from the C-terminus of the oligomer attached, or immobilized, respectively, within the recess of the substrate, using respectively sorted particles, i.e. only particles containing the first molecule, or with limited mixtures, such as with two particles each having a different first molecule, while at the other coupling levels a plurality of variants is generated. With such focused oligomer libraries sequentially a plurality of oligomer variants can be produced that all contain a particular epitope, or structure feature, respectively, that can then be investigated specifically for determining a suitable binding partner. Since herein the epitope already allows a binding to the binding partner, possibly by the variation of the remaining molecules within of the respective monomers an improved binding to the binding partner may be provided.

As an example the flag epitope of a length of 15 amino acids (XXXXDYKD/EXXDXXXX) can be used. Respective peptide variants can be produced which all bind to the flag M1 antibody, and these can be investigated for such peptides the binding of which to the antibody can be switched for instance by different temperatures or selectively influenced by light.

Thus new application for oligomers, such as peptides within the array format can used in particular in research and/or diagnosis (reading of antibody connections or antibody profiles of patients) or within the pharmaceutical industry (circular peptides in particular are suitable for searching for binders for proteins and for therapeutics, as well as for reading binding epitopes of antibodies that recognize the conformative epitopes).

The substrates or carriers, respectively, of the arrays can be produced from various materials such as glass, quartz, silicon, ceramics, plastics, metals and/or composite materials. Herein all materials are resistant against the chemicals that are used within the combinatorial synthesis. Within the peptide synthesis these are preferably the solvents N-methyl-2-pyrrolidone (NMP), dimethylformamide (DMF), acetone, dichloromethane, ethanol, water as well as diisopropylamine and acetic acid anhydride. For the separation of the peptides at least 50% trifluoroacetic acid (TFA) within a suitable solvent, such as isopropanol, methanol and dichloromethane is suitable. In addition the materials must allow the microstructuring, that means the generation of suitable recesses. The microstructuring of the glass surfaces can for instance be performed using a suitable lithographic method, such as by means of a dry or wet-etching process. Advantages of the plastic materials rest in the possibility of a fast replication of the microstructured substrate for instance by means of hot stamping. Suitable materials are known to the skilled person.

The variety of the possible materials comes from the fact that the filling of the recesses with particles containing the monomers does not demand transparency and any positioning of the substrates at all. Preferably the substrate is a substantially non-transparent or opaque material, respectively. Only the possibility of the detection of the deposited particles after the deposition, i.e. the placing within a specific recess, as well as the derivatization of the surface with functional groups for a solid-phase synthesis is of importance. Particles containing monomers or first particles, respectively, comprising a first molecule, can be produced by different methods. The function of the particles is to transport monomer components, or first molecules, respectively, for the combinatorial synthesis to the synthesis location.

For instance polymer particles can be utilized having embedded monomers that after the melting of the polymer matrix may take part at the coupling reaction at the surface. Such particles can be produced by means of emulsion, painting or spray-drying methods. Both methods allow particle dimensions within the micrometer range. For obtaining a magnitude distribution of the particles after the particle production additional process steps, such as sieving or screening, can be performed. Respective sieves or screens are known in the prior art. If particles within the submicrometer range shall be produced, usually sieving and screening methods come to their limits. This can be avoided by using fine particles which are always present within the spray-drying process and that have a diameter of less than 1 µm. Due to adapted magnitude of the recesses thereafter only these fine particles will get into the recesses. All larger particles are automatically removed from the substrate surface during application, or during application of the particles onto the substrate surface, respectively, such as by placing the molecule-containing particles onto the substrate surface. Common screening processes usually cannot be used for producing such fine particles.

Alternatively also composite particles can be used having a core already produced by a different method, and the surface of which is occupied with monomers, or molecules, respectively. For instance an anorganic core of silicon dioxide can be provided which is surrounded by a shell of the polymer matrix with the embedded monomers, or molecules, respectively. An advantage of these particles rests in the monodispersity and in their spherical shape.

The preparation of particles with irregular dimensions can also be obtained by means of microstructured surfaces. The recesses are filled with solid substances, such as with polydispersed polymer particles, and are subsequently heated, so that the substance obtains the shape of the recess. The removal of the particles can for instance be done by means of ultrasound. Alternatively, the recesses can be filled with liquid materials, wherein the molecules/monomers as well as the particle matrix are dissolved within solvents, such as dichloromethane. After the drying step in the recesses there have formed homogenous monomer-containing particles.

The present invention substantially relates to three variants of the random deposition of particles. On the one hand particle mixtures can be placed within the recesses randomly, wherein the different particles are marked. Alternatively, a sequential random particle deposition without a marking of the particles can be performed. In addition a combination of the two variants mentioned above is possible.

According to the first variant the marking of the particles with colorants, fluorescence markers or by means of the shape of the particles is performed. This may for instance also be reached in that the monomer particles are luminescent or are provided for instance with oligonucleotide markers that can be detected by hybridization. Such techniques are well-known to the skilled person. Important for the determination of the position herein is only that each kind of monomer particles can be clearly differentiated from different monomer particles. If this condition is fulfilled, all different kinds of particles are mixed and are placed onto the surface within the recesses with surplus. Thereafter all recesses are filled randomly with particles by rubbing the particles within the dry state or by means of a carrier fluid into the recesses. By reading the marker subsequently it is determined which monomer, or which particle respective, is deposited in which recess. Variant 1 herein has the advantage that all monomer particles necessary for one layer are applied in a single step and in this way fast and very reliably (since a surplus of particles can be used) and can be placed on the substrate surface very easily.

According to variant 2 the particles are applied randomly onto the substrate surface within the recesses, wherein only a part of the recesses is filled. The sequential filling of the recesses with different monomer particles leads to a complete filling substantially of all recesses. By detecting the deposition locations of each monomer particle after the filling of the recesses explicitly the information is determined which monomer was deposited in which recess. With twenty monomers thus twenty detection processes must be performed. Variant 2 herein has the advantage that it does not need any markings of the particles and/or of the first molecules. However, a marking of the particle with for instance a fluorescence marker can facilitate the determination of the location of deposition.

In addition for the random deposition also a combination of both variants is suitable. If herein three markers are used for the particle marking, then the number of random placing steps is reduced by the factor 3. Apart from the surface with for instance cylindrical recesses also different geometries, such as honeycombs or channels can be used for a particle deposition.

Marked particles can be produced by a variety of different methods. Usually particles can be produced by using an air jet milling, spray drying, casting, or melting, respectively, within molds. The marking can be done already during the production or subsequently. Colorants, fluorescent or luminescent molecules or nanoparticles, such as quantumdots, can be added already during production of the particles which to this end should have preferably two characteristics: They should not impair the solid-phase synthesis (for instance the added marker reagents during peptide synthesis should have no free amino groups or SH groups that react with the C terminal activated monomer components) and in addition they should not impede the formation of the particles (for instance metallic or ceramic nanoparticles may plug the nozzle of a spray dryer). Suitable colorants are known to the skilled person.

These conditions however only hold up to a certain amount, or even not at all, respectively, since for the marking of the particles in some circumstances only very small amounts, for instance of fluorescent colorants, are necessary, so that it may be advantageous to specifically couple to the C terminal activated in large excess amino acid components for binding the fluorescent colorants in a subsequent step to the already preformed particles. This may for instance serve to allow a marking of preformed monomer particles also in a subsequent process in that the particles for instance are briefly incubated within a possibly warmed-up aqueous and/or alcoholic solution, such as ethanol which also contains the respective colorant.

The deposition of the particles may occur with many different methods that are known to the skilled person. A particularly simple and preferred method herein uses dry particles that are rubbed into the recesses of the substrate using a lint-free paper. When herein the particles are present in excess, then thereby an almost 100% occupation rate can be reached, i.e. at least in 90% of the recesses there is a respective particle, preferably 95% or more, 98% or more, or 99.5% or more. When the particles have a dimension adjusted to the recess, i.e. that only one particle can be placed in one recess, then also it can be easily reached that within each recess thereafter a particle is placed. An adjusting of the dimension can be easily reached: The particles must be so small that only one particle fits into one recess and they must be so large that two particles do not fit into a recess. Alternatively, the particles may also be suspended within a liquid and may be rubbed into the recesses.

An almost complete and very simple placement of particles out of liquids into micro cavities or even nanocavities works until to dimensions of several hundred nanometers particle diameter, in particular if a meniscus, that is specifically defined and that retracts above the surface of the cavities, really drives the particles from air into the cavities. The placement, or the deposition, respectively, of particles within cavities, or recesses respectively, of different size is for instance shown in Yadong Yin et al., Template-Assisted Self-Assembly: A Practical Route to Complex Aggregates of Monodispersed Colloids with Well-Defined Sizes, Shapes, and Structures, J. Am. Chem. Soc. 2001, 123, 8718-8729, the content of which is fully incorporated herein by reference.

The deposition of particles with different occupation rate can be realized either by setting the particle concentration within a solution or within an aerosol or by using special rollers. By varying the concentration of the particle mass within a solution occupation rates of 0.01-100%, such as e.g. 1-99%, 5-95%, 10-90%, 20-80%, 30 to 70%, 40 to 60%, or 45-55%, respectively, can be reached.

By a microstructuring of the roller the contact surface between the roller and the substrate is reduced. Only the particles at the contact surface are transferred, while particles that do not have contact to the substrate, remain on the roller. Thus, the occupation rate can be easily adjusted by fitting the roller relief. The elasticity of the roller herein may influence the quality of the deposition: With an elastic roller particles that lay on a smooth surface will always remain on the roller surface, since by the pressure of the roller the contact surface between the latter and the particle increases. On the other hand those particles that lay within the recesses lose the contact to the roller and thus remain in the recesses.

For detecting the particle deposition methods are used that can recognize the marking of the deposited particles as simple and as fast as possible. Herein high-resolution camera systems, scanners, luminescence and fluorescence scanners, or scanning microscopes are used. The major advantage of the camera system is the fast detection of the deposited particle patterns. In this case a camera system having a wide field of view could be utilized which at the same time has the necessary resolution for a safe detection of single spots. E.g. camera chips available on the market having up to 200 megapixels with more than 100 pixels per spot, can be used, if 1 cm$^2$ is imaged with a distance between two recess centers, or a pitch, respectively, of 10 μm. Herein the shape, the color, the time sequence of the deposition, the fluorescence or the luminescence of the particles, the strength of the respective signals and all conceivable combinations of these characteristics can be determined. It is only important that this method reliably recognizes the respective locations and the different identities of the particles.

When marking the protective groups with colorants, the synthesis locations have distances from each other that are by magnitudes smaller than the wavelength, and thus can only be determined using special fluorescence techniques. To this end for example superresolution microscopy such as PALM, STORM and dSTORM can be used. The distance between two adjacent spots can be controlled by the concentration of the monomers.

There already exists a whole variety of known applications for peptide arrays. These include parallelized diagnoses. Other already known applications divide the protein sequences of a known antigen protein into overlapping peptides to find out to what substructures of the protein (epitopes) a monoclonal or polyclonal antibody binds.

In addition there is the possibility to perform stochastical assays using the stochastical oligomer arrays according to the invention. To this end a fissible linker is inserted between the oligomer and the recess, i.e. the second molecule is a linker that can be separated. For instance by means of the stochastical assays the effect of peptides onto bacteria and onto proteins can be investigated.

To this end after the synthesis of the oligomer array a sample to be investigated can be applied onto the array. The sample is a liquid sample, such as for instance a solution with bacteria, solved proteins or other samples to be investigated. The recesses are filled with the liquid. An excess of a solution can be removed, so that due to the surface tension of e.g. aqueous solutions, within the recess there is formed a liquid reservoir that is arched into the direction of the opening of the recess (concave or convex meniscus). If now a top plate, such as of glass, is positioned above the substrate within a defined distance, then the liquid reservoirs enter into a connection with the top plate. Thereafter the fissible linkers can be separated e.g. by UV light and the effect of the separated oligomers onto the bacteria, the proteins or the introduced medium can be investigated. Herein the top plate serves two functions. On the one hand by the plane surface a detection of the interactions to be investigated is made possible. On the other hand the top plate diminishes an evaporation of introduced solution due to its small distance to the substrate.

The expression "comprising" within the scope of this invention refers to an open listing and apart from the components or steps, respectively explicitly mentioned does not exclude other components, or steps, respectively. When in the scope of the present invention a composition is described using the term "comprising" this explicitly also includes compositions that consist of the mentioned components or essentially consist of the mentioned components.

The expression "consisting of" within the scope of the present invention refers to a closed listing and apart from the explicitly mentioned components, or steps, respectively excludes any different components, or steps, respectively.

The term "essentially consisting of" or "substantially consisting of" within the scope of the present invention refers to a partially close listing and refers to compositions that apart from the mentioned components only comprises such further components that do not materially alter the characteristics of the of the composition or that are present in such amounts that do not materially alter the characteristics of the composition.

BRIEF DESCRIPTION OF THE DRAWINGS

Further features and advantages of the invention can be taken from the subsequent description of preferred embodiments with reference to the drawings. In the drawings show:

FIGS. 7a and 7b show an example of marking monomer particles using fluorescent colorants: light microscope picture (FIG. 7a) and fluorescent picture of randomly deposited particles (FIG. 7b). The location of the monomers is identified using the fluorescence signal (red, green). Unfilled recesses are used for the deposition of subsequent monomers. Pitch 10 µm;

FIG. 8 shows the dipeptide array according to example 2 with random arrangement of the monomers with fluorescence marking;

FIGS. 9a, 9b, 9c, 9d, 9e and 9f show the evaluation of the dipeptide synthesis according to FIG. 8;

DESCRIPTION OF PREFERRED EMBODIMENTS

Figure 1:
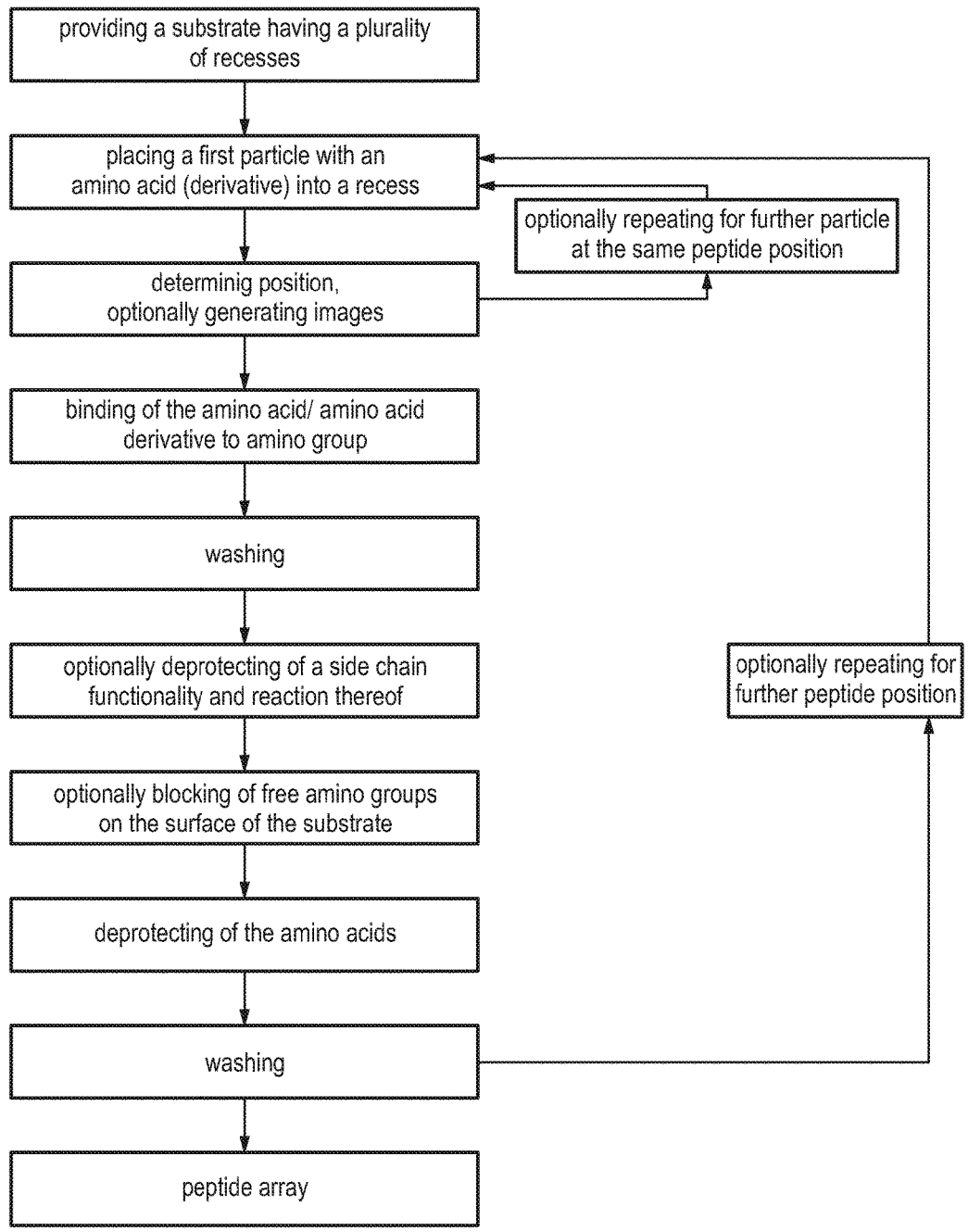
FIG. 1 is a schematic representation of the method steps for producing a peptide array.

In one embodiment the first molecule is an amino acid and/or an amino acid derivative.

The amino acid/the amino acid derivative reacts with the second molecule by forming an amid. The second molecule may also be an amino acid and/or an amino acid derivative, however the second molecule may be a surface functionality on the substrate surface, in particular within the recess of the substrate, or a functionality respectively, at one end of a spacer which at the other end of which is present immobilized within a recess of the substrate. Usually the reaction of the first molecule with the second molecule is a coupling reaction with the formation of an amide binding. Also the surface functionality or the functionality at one end of a spacer usually is a carboxyl group that reacts with the N-terminus of the first molecule forming an amid. Thus on the substrate surface there is formed a peptide directly or indirectly via a spacer. Preferably the peptide is formed according to peptide solid phase chemistry that is known to the skilled person.

Amino acids, or amino acid derivatives, the synthesis and reactions of which are well-known to the skilled person. For a coupling reaction, i.e. the reaction of the N-terminus of an amino acid/an amino acid derivative with the C-terminus of a different amino acid/a different amino acid derivative the amino group of the amino acid/the amino acid derivative (i.e. at the $N_\alpha$-position) must be protected, since otherwise the amino acid/the amino acid derivative possibly reacts with itself. After the coupling reaction this protective group can be preferably fissible and under mild conditions, so that a further coupling can occur. The synthesis of peptides is performed from the C-terminus to the N-terminus. As temporary a amino protective groups there are two urethane-protective groups in use: tert-butoxycarbonyl (Boc) which in acid surroundings can be divided using protons, and fluorenylmethoxycarbonyl (Fmoc) which can be separated by reaction with secondary amines. If necessary for avoiding secondary reactions or for the synthesis of specific peptide, then the functional groups in the side chain of amino acids are additionally protected by suitable protective groups (see e.g. P. G. M. Wuts, T. W. Greene, Greene's Protective Groups in Organic Synthesis, 4. Auflage, Juni 2006, Wiley) wherein in the first line Arg(Tos), Arg(Mts), Arg(Mtr), Arg(Pmc), Asp(OBzl), Asp(tert-But), Cys(4-MeBzl), Cys (Acm), Cys(SBut), Glu(OBzl), Glu(OBut), His(Tos), His (Fmoc), His(Dnp), His(Trt, Lys(CI—Z), Lys(Boc), Met(O), Ser(Bzl), Ser(But), Thr(Bzl), Thr(Bzl), Thr(But), Trp(Mts), Trp(CHO), Tyr(Br—Z), Tyr(Bzl) or Tyr(But) can be utilized.

Within the scope of the present invention the peptides can be produced using well-known methods of the peptide chemistry, see for instance HoubenWeyl, Methoden der organischen Chemie, Band 15/2, also B. Merrifield, J. Am. Chem. Soc. 85, 2149 (1963) or R. C. Sheppard, Int. J. Peptide Protein Res. 21, 118 (1983), the contents of which are fully incorporated herein by reference.

A "protective group" as used herein refers to a molecule that reacts with one or more specific functionalities of a first molecule or of a second molecule so that this functionality is insensitive to a different reaction with respect to a modification/elongation of the oligomer. By selecting suitable reaction parameters the release of the protective group can occur under suitable conditions. Preferably the detectable marker at the same is a protective group, whereby the synthesis of the oligomer is simplified and additional reaction steps can be avoided. The protective group chemistry for producing oligomers, or specific reactions or a reaction avoidance, respectively, of side-chain functionalities is well-known to the skilled person.

One possibility for the synthesis of the peptide array according to the invention is shown in FIG. 1. To this end a substrate having a plurality of recesses (more than $10^6$ spots/cm$^2$) is provided. A monomer particle, i.e. one (single) particle is placed with an amino acid, or an amino acid derivative, respectively, within a recess. Preferably the monomer particle with the amino acid/amino acid derivative contained herein is provided in such a way with a detectable marker that by an image, preferably by means of a fluorescence image, the identity of the amino acid, or the amino acid derivative, of the recess and thereby the position on the substrate can be assigned. Preferably this is repeated for one or more monomer particles (each) with a different amino acid, or amino acid derivative, respectively. The amino acid, or the amino acid derivative respectively, is bound to amino groups that are already present on the substrate surface in immobilized form. The amino groups on the one hand may present the N-terminus of an already immobilized amino acid, or of a peptide, respectively, or a surface functionality that is directly or indirectly present by means of a spacer on the substrate surface within a recess. By washing the polymer matrix of the monomer particle unbonded amino acids and other contaminations are removed. The side-chain functionalities of the amino acids, or the amino acid derivatives, respectively, can be deprotected and can be reacted with further substances, such as amino acid, or amino acid derivatives. If a first layer of amino acids, or amino acid derivatives, respectively was applied onto the substrate, then the free amino groups on the substrate surface are blocked. The substrate is washed again. Subsequently the repeated deposition of monomer particles occurs for forming a further peptide position, until the peptide reaches the desired length.

Figure 2:
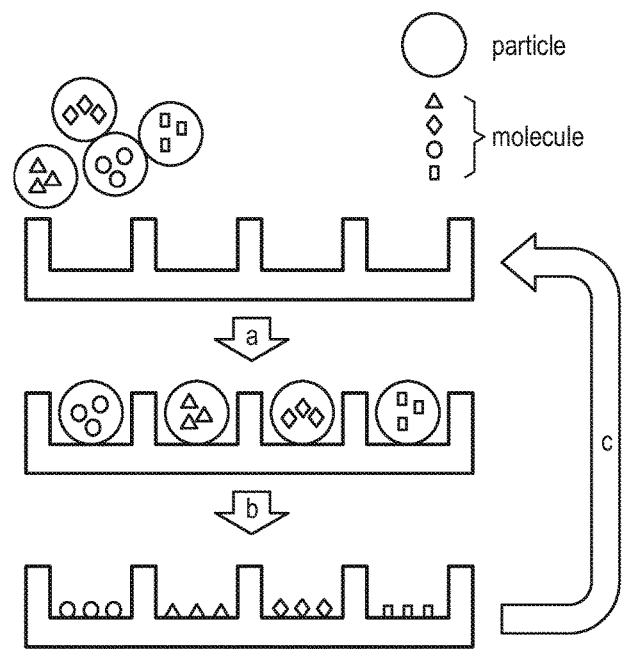
FIG. 2 is a schematic representation of the placing of different first particles with a respective first molecule within a recess of a substrate and of the release of the first molecule from the first particle.

From FIG. 2 the placing of monomer particles within which there is received a molecule each, can be seen. Step a shows the random placement of the respective particles within a recess of the substrate. Step b shows the immobilization of the molecules at the substrate surface. It can seen that the use of particles, and in particular of monomer particles allows a specific transfer of a molecule into a specific recess and thus does not only allow to determine the identity of the molecule, but also the position on the array explicitly. The present steps are repeated for each molecule layer (step c), until the polymer array has reached the desired length.

Figure 3:
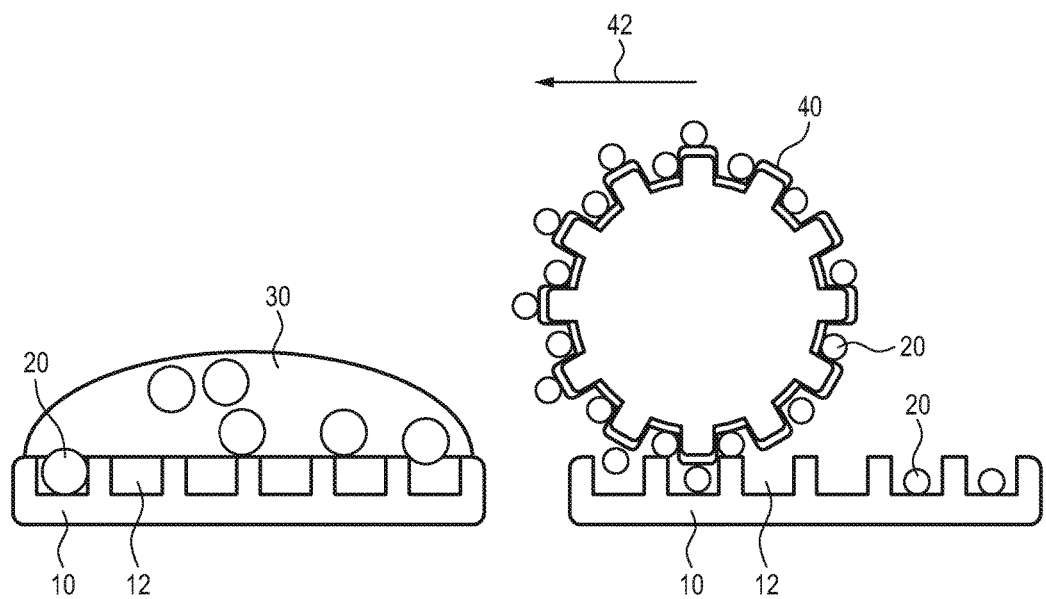
FIG. 3 illustrates deposition methods for reduced occupation rates: minimization of the concentration of the added particles within solution (left side) and the stochastical application by means of a microstructured roller (right side)

The placement of the particles preferably is done stochastically. FIG. 3 shows two possibilities how the particles can be placed within the recess 12 of a substrate. Herein the particles preferably are monomer particles, i.e. a particle comprises only a particular molecule, such as glycine. Such monomer particles are preferred, since other monomer particles, i.e. particles having a different monomer, such as biotin, usually are applied sequentially, whereby the detection of the kind of monomer and the position of which on the array is simplified. In addition herein the number of detectable markers can be reduced. Alternatively, mixtures of monomer particles can be used, for instance a first particle with a first molecule, such as glycine, and a different first particle with a second molecule that is different from the first molecule, for instance biotin. A further possibility is to use particles that comprises several different molecules.

In the left figure the particles 20 are suspended within a liquid 30, for instance in water or a different solvent. After applying the suspension the particles for instance can be rubbed into the recesses 12 using a cloth or a wiper. As shown in the right figure, the particles 20 can optionally be placed within the recesses 12 of the substrate using a roller 40. The roller 40 herein comprises a microstructured surface with dimensions that substantially correspond to the dimensions of a recess within the substrate. The microstructured surface for instance comprises elevations, recesses and distances therebetween, with a dimension corresponding to the particle size or a larger size, for instance 10% larger dimensions or more, such as 25% larger dimensions or more, 50% larger dimensions or more, 100% larger dimensions or more, or 500% larger dimensions or more. By turning or rolling 42 the roller the particles 20 can be placed within the recesses 12.

In one embodiment the first molecule of the first particle comprises an amino group with an amino protective group and a free carboxyl group.

In one embodiment after step (d) the amino protective group is removed.

In one embodiment after one of steps (b), (c) and (d) a detection of the detectable marker is performed depending on a position of the recess on the oligomer array.

Preferably the detectable marker is determined after step (b). In this case the detectable marker preferably is present at and/or within the particle. More preferably the detectable marker is only embedded within the particle.

In case the detection of the detectable marker is done after step (c) and/or (d), the detectable marker is usually bound covalently to the first molecule. Herein the marker functions preferably also as a protective group. It should be clear that the detectable marker must be removed before a possible successful elongation of the oligomer, to not impair the detection of the first molecule within the subsequent step.

As already mentioned before, several detectable markers, such as 2, 3, 4, 5, 6, 7, 8, 9, 10 or more, can be used. These detectable markers can also be used in different concentrations. In addition a combination of detectable markers may be present on the surface of the particle, while the first molecule usually preferably does not comprise a detectable marker, to not impair the coupling reaction with the second molecule (possibly due to steric grounds). However, it can be advantageous to mark the first molecule. Herein mainly detectable markers of small space dimensions are preferred, such as radioactive detectable markers. Radioactive markers have the advantage that they can be received within the first molecule and thus can form a component of the first molecule.

In one embodiment step (f) comprises the generation of a 3D deposition mask from the determinations of the detectable marker depending on the position of the recesses on the oligomer array.

The 3D deposition mask can be generated from all images that are generated for determining the detectable marker. This preferably is done automatically, for instance by means of a computer and a suitable computer program. The 3D deposition mask is the information on the exact position of each respective oligomer, for instance the oligomer is assigned to a recess or its position on the substrate is determined for instance by means of a coordinate system. In addition the sequence of the individual molecules of the oligomer and the identity thereof are determined. In addition also other information may be contained within the 3D deposition mask, such as possibly performed ring closures and/or side chain modifications of individual oligomer molecules.

In one embodiment after step (d) a chemical modification of the immobilized oligomer occurs, wherein a chemically modified oligomer is obtained.

Such chemical modifications are known to the skilled person and comprise ring closures between individual molecules of an oligomer and/or side chain modifications. Side chain modifications contain a reaction of a side chain of a first molecule after a coupling reaction with one or more further molecules. In this way for instance branched oligomers can be generated, or particular functionalities can be included in the oligomer.

Reaction partners that are used for a chemical modification and that shall be included in an oligomer to be synthesized, preferably also are placed within the recess by means of a particle. This has the advantage that possibly also the chemical modification can be determined by means of a detectable marker.

Within one embodiment the detectable marker is a removable detectable marker that can be detected by means of optical systems, such as by light microscopy.

Such markers are known to the skilled person. Suitable detectable markers are for instance described in WO 2015/066400, the contents of which are fully incorporated herein by reference.

In one embodiment the first particle comprises a polymer matrix within which the first molecule is embedded.

The polymer matrix may consist of a polymer or of a mixture of several polymers. Preferably it is a styrene-acrylate copolymer. The polymer matrix may be generated in different shapes, preferably substantially spherical or globular, respectively, with variable dimensions, or diameters, respectively.

According to the production methods that are known to the skilled person particles with variable diameters can be obtained. In this case particles with undesirably small diameters are removed. This may for instance be done by centrifuging. Too large particles usually do not present a problem, since these do not fit into the recesses of the substrate and thus do not take part in the reaction, and can for instance easily be removed by the application of pressurized air.

If within the present invention reference is made to a median diameter, this comprises a size distribution within which at least 90% or more, preferably 95% or more, such as 98% or more, 99% or more or 99.5% or more, of the particles have the given diameter. The remaining particles, i.e. the difference to 100%, preferably have a deviation from the median diameter of ±50% or less, such as for instance 35% or less or 10% or less. If for example particles with a median diameter of 3 μm are described, then 90% or more of the particles have a size of 3 μm. The remaining 10% or less have a size distribution in the range of 1.5 μm to 4.5 μm.

The synthesis of the polymer particles preferably is performed so that the first molecule is received therein. Preferably herein the first molecule is a monomer. However, the first molecule itself may be a further oligomer, such as a dimer, a trimer, or a tetramer so that the oligomer to be synthesized is elongated by the further oligomer, such as by the dimer, the trimer, or the quatromer. This has the advantage that conserved regions within the oligomers of the oligomer arrays are generated, i.e. regions that are identical in all oligomers of the oligomer arrays. The first molecule in addition can be provided with a protective group and/or a detectable marker.

The particle with the first molecule, preferably with a first molecule embedded therein, can be placed within the recesses of the substrate by simple techniques, such as by wiping. The polymer matrix becomes permeable, i.e. perforated and/or is dissolved, by the influence of temperature for instance (heating) and/or by chemicals, and the first molecule contained therein is released.

The processing of suitable polymer matrices and of the molecules received therein can for instance be taken from WO 2014/169928 A1, the contents of which are fully incorporated herein by reference.

In one embodiment the method for producing the oligomer array comprises the following steps: a) providing a substrate with a plurality of recesses; b) stochastic placement of a first particle with a first molecule within a recess; c) releasing the first molecule from the first particle; d) binding the first molecule to a second molecule while forming an oligomer, wherein the second molecule is immobilized within the recess; e) optionally repeating the steps (b) to (d) while elongating the oligomer; wherein at least a first particle and/or a first molecule comprises a detectable marker. Herein a plurality of first particles is present. Preferably each first particle comprises identical first molecules, i.e. in a particular first particle there are identical first molecules, while in a different first particle first molecules may be present which are different from the first molecule of the first determined particle. More preferably each first particle comprises a detectable marker that indicates the first particle according to the first assigned molecule. The sequence of steps b), c) and d) thus describes the structure of a layer of the arrays, while the optional step e) describes the structure of one (or more) of the following layers.

Between the steps b) and c) preferably there are the following steps: b)i) detecting the position of the first particle and b)ii) repeating the steps b) and b)i), until substantially all recesses are filled with a first particle. The optional repeating of the steps (b) to (d) thus includes a repeating of b), b)i), b)ii), c) and d). This alternative embodiment herein reflects the second variant mentioned above according to which there is dispensed with the marking of the first particle and/or the first molecule. This is made possible by releasing in step b) only a defined first particle with a defined first molecule, so that in step b)i) the future location of deposition of a defined, i.e. known, first molecule is precisely determined. This is performed in step b)ii) for all different kinds of first particles and thus for assigned first molecules, until substantially all recesses are filled. The sequence of steps b), b)i), b)ii), c) and d) thus describes the structure of a layer of the array, while the optional step e) describes a structure of one (or more) following layers. It should be clear that a filling of "substantially" all recesses with a first particle describes the desired filling degree which can be varied according to the requirements. Thus for instance it can be desired that not all recesses are filled, and thus in particular recesses there is not performed an elongation step, whereby an oligomer array with different oligomer lengths can be obtained.

In one embodiment in step (b) the placing of a single first particle with a first molecule into a single recess is performed. Thus the recess has a cross section and a depth so that a single particle fits into a single recess. Thus there is a single particle within a single recess. This by means of the determination of the detectable marker allows to specifically assign the particle to a recess and thus also to assign the first molecule. Preferably the first molecule is configured as one or more identical first molecules, such as for instance two or more identical first molecules, more preferably two to eight identical first molecules. Thus within a determined first particle several first identical molecules are present, whereby in a different first particle several first identical molecules are present which are different from the several first identical molecules of the determined first particle. A determination of the passing of a single particle into a single recess preferably is performed during production of the oligomer array according to the invention, i.e. during detection of the detectable marker.

In one embodiment step (c) and/or step (d) of the method according to the invention is done while a solvent is present within the vapor phase. Thus the release of the first molecule from the first particle, or respectively from the first particle and/or the binding of the first molecule respectively are done at the presence of a solvent in the vapor phase. To this end the substrate is exposed to an unsaturated and/or saturated vapor atmosphere of the solvent. The vapor condenses at the surface of the substrate and/or is absorbed by the first particle. Thereby the polymer matrix becomes penetrable, i.e. the polymer matrix becomes perforated and/or is dissolved, and the first molecule contained therein is released, or the first molecules, contained therein are released, respectively. By contrast to a single release by temperature increase thereby on the one hand considerably larger amounts of molecules can be released, and on the other hand released molecules can diffuse more simply to the reactive groups on the substrate. Herein the solvent preferably is configured as one or more organic solvents, such as dichloromethane, acetone, N,N-dimethylformamide and/or combinations thereof. The solvent is placed within the recess and warmed thereafter. Preferably the recesses are exposed to the solvent vapor. The extraction of the molecules can be done at temperatures between −20° C. and +110° C., preferably 10 to 80° C., more preferred 60 to 80° C. Higher temperatures of for instance >80° C. to 110° C. usually facilitate the extraction and binding of the molecules. Lower temperatures of e.g. −20° C. to <10° C. impede the diffusion of the molecules during extraction. This extraction may take between 1 minute and 90 minutes, preferably 20 to 60 minutes.

In one embodiment a surface functionality on lands between individual recesses is chemically varied. Preferably this is done within the frame of the immobilizing of the second molecule wherein the latter has the surface functionality. The immobilization of the second molecule herein occurs not only within the recesses, but over the total substrate. The second molecules immobilized in this way subsequently are modified depending on the location of immobilization so that the physiochemical characteristics of the lands between the recesses and the recesses itself vary. The surface of the lands between the cavities can be modified so that it impedes the diffusion and thus the binding of the first molecule out of a cavity to the adjacent cavities.

For instance this modification of the surface between the lands can occur by means of etching the surface of the lands, wherein the recesses themselves are not exposed to the etching medium. The recesses on the one hand can be protected from the etching medium for instance by means of a polymer matrix which is placed within the cavities before the etching process and is sintered for reaching a homogeneous filling. Alternatively the surface within the recesses can be protected against the etching medium by means of a sputtered metal layer. To this end the total substrate is covered with a metal layer which subsequently is removed from the surface of the lands.

The etching for instance can occur using a cleaning plasma (oxygen, nitrogen or argon plasma or different gas plasmas) or by means of a liquid medium of a strong acid or base. The single condition is that that the material protecting the cavities is chemically inert against the etching medium that is used. Once the etching of the surface of the lands has ended, the material protecting the recesses is moved from the recesses. The for example used polymer matrix herein can be removed by suitable organic solvents that are known to the skilled person. A metal layer can be removed by anorganic solvents that are known to the skilled person.

After the etching of the surface of the lands between the cavities has been performed, the surface of the lands can be chemically modified. For instance hydrophobic silanes can be coupled to the OH groups generated during the etching process. Thereby the diffusion of the molecules between the individual cavities during the extraction can be impeded. Apart from the possibility of the etching there is the possibility to modify the surface of the lands by means of activating photosensitive groups. To this end onto the surface functionality of the total substrate there is coupled a photosensitive linker which can be separated by means of exposure to UV light. This exposure for instance can be done by means of a so-called mask aligner such as known in semiconductor manufacture. After the division of the linker on the lands between the cavities this surface can be made water-repellent, whereby the diffusion of the molecules between the individual recesses during the extraction the later occurs is impeded. Subsequently to the hydrophobizing the photosensitive linker is separated in the cavities. Thereafter step (b), the placing of a first particle with a first molecule within a recess, can be performed, and the further steps can be performed.

In one embodiment at least one recess is sealed during step (c) and/or step (d) of the method according to the invention. Thus the recesses are sealed during the step of the release of the first molecule from the first particle and/or during the step of binding the first molecule to a second molecule while generating an oligomer. This impedes the diffusion of the first molecule, or of the first molecules, respectively, out of the recesses and a contamination of other recesses, or a lower rate, respectively, coincident therewith. Herein the sealing can be performed by applying a sealing material onto the substrate surface. The sealing can be effected by the contact of the sealing material and the substrate surface. Thus each cavity is a closed system within which the release and/or the binding of the molecule, or of the molecules, respectively, are totally independent from the other cavities of the substrate. As a sealing material for instance PDMS, PTFE, PFDV membranes and other commercially available adhesive tapes may be used. Alternatively or in addition each other method step, wherein an isolation from the environment is desired, also can be sealed accordingly, i.e. by sealing the recess. Also the storage of the oligomer array can be done so that preferably all recesses are sealed.

In one embodiment a second molecule is immobilized within the recess, wherein the second molecule is a fissile or cleavable spacer. Thereby fissile spacers can be included within the synthesis of the oligomer array. The synthesized oligomers can be simply separated and possibly transferred onto a target surface or into a recess of a substrate. This in addition allows for a cleaning of the oligomers, since preferably only fully synthesized oligomers are transferred. The residual products (not fully synthesized oligomers) on the other hand preferably are not transferred and can be removed during a washing step. Complete oligomers are those oligomers that have a chain length according to the number of processed steps according to the present methods, i.e. the number of monomers of the oligomer to be obtained. In addition the oligomer arrays can be replicated by the transfer. By controlling the percentage fission rate thus several replicates of the same oligomer array can be reached.

The separation of the molecules is reached by incorporating fissible spacers at the basis of the oligomers. Such spacers that can be safely separated for instance by means of light, in particular UV light or by hydrogenolysis or photolysis or under basic conditions etc. as well as under reaction conditions of a synthesis, are known to the skilled person. Selectively fissile linkers that may be based on a methionine or an ester group can for instance be taken from DE 69435011 T2. Fields G B and R L Noble, 1990, Solid phase peptide synthesis utilizing 9-fluorenylmethoxycarbonyl amino acids, Int. J. Pept. Protein Res. 35: 161-214 also discloses further linkers of this kind. Examples of further spacers are the rink amide linker or the UV fissile linker which can be taken from M. S. Bernatowicz, S. B. Daniels, H. Köster, Tetrahedron Lett. 30 (1989) 4645 or Stefan Peukert and Bernd Giese, The Pivaloylglycol Anchor Group: A New Platform for a Photolabile linker in Solid-Phase Synthesis, J. Org. Chem. 1998, 63, 9045-9051.

In one embodiment the synthesized oligomers, preferably the fully synthesized oligomers, are transferred onto a target surface. As mentioned above complete oligomers are those oligomers that have a chain length according to the number of steps performed according to the present method, i.e. according to the number of monomers of the oligomers to be obtained. The target surface can be a recess of a different, second substrate having a plane surface, such as an object slider, a membrane or any different container. For the transfer the cavities are filled with a buffering solution. The composition of the buffer depends on the characteristics of the synthesized oligomers and is known to the skilled person. To impede the diffusion of the oligomers occurring during transfer from one cavity into adjacent cavities, as the target surface for instance a membrane can be used which seals the individual cavities. After the placing of the membrane the separation of the spacer is performed. All oligomers (fully synthesized oligomers as well as residuals) now can move freely within the cavities filled with the buffering solution within the boundaries of the diffusion.

To preferably transfer only the completely synthesized oligomers and to thus obtain a cleaning of the oligomer array, in the last step of the oligomer synthesis a functional group is coupled to the terminal groups of the oligomers. This for instance according to the solid-phase synthesis according to Merrifield can only couple to completely synthesized oligomers, since the decomposition products have already been acetylated (blocked). These functional groups can enter a binding with the target surface which is also functionalized. Examples of these bindings are biotin streptavidin, azide-alkyne or thiol-gold interactions. After the separation of the synthesis products only completely synthesized oligomers will enter the binding with the functionalized target surface, while the decomposition products are washed way. Suitable functional groups are known to the skilled person.

In one embodiment the synthesized oligomers, preferably the fully synthesized oligomers, are brought into contact with a sample. This allows the possibility to directly investigate the fully synthesized oligomer array with respect to the individual oligomers. Thereby stochastic assays can be performed with the stochastic oligomer arrays according to the invention. For instance by means of the stochastic assays the effect of peptides onto bacteria or proteins can be investigated. The sample may be any kind of sample, preferably it is a liquid sample, more preferred samples that contain a body fluid, such as blood, serum or urine. The samples can be used directly or in diluted form. The assay can be done directly within the recesses.

For preferably simplifying the interaction of the fully synthesized oligomers with the sample, or to make the latter possible at the beginning, respectively, a fissile linker between the oligomer and the recess may be present, i.e. the second molecule is a fissible linker. The recesses are filled with the sample. An excess of solution can be removed, so that due to the surface tension of for instance aqueous solutions within the recess there is formed a liquid reservoir arched into the direction of the opening of the recess (concave or convex meniscus). If now a top plate, for instance made of glass, is positioned within a defined distance above the substrate, then the liquid reservoirs enter into a connection with the top plate. Thereafter the fissile linkers may be separated for instance by means of UV light, and the effect of the separated oligomers onto the bacteria, the proteins or the introduced medium is investigated. The top plate herein fulfills two functions. On the one hand a detection of the interactions to be investigated is made possible by the plane surface. On the other hand the top plate due to its small distance to the substrate avoids an evaporation of the introduced solution.

In one embodiment the oligomer array is a focused oligomer array.

Such a focused oligomer array contains preserved regions, i.e. one or more monomer molecules that are identical in all oligomers of the oligomer arrays. It was found that the method according to the invention is inter alia suitable for the generation of such a focused oligomer array.

In one embodiment the oligomer array comprises a 3D deposition mask which allows to assign at least one first molecule and the second molecule to the 3D deposition mask to a position of the recess on the oligomer array.

In one embodiment a first (terminal) molecule comprises a detectable marker.

A detectable marker can be any kind of marker, such as a luminescent marker, a fluorescence marker, markers detectable by means of hybridization, but also radioactive markers. Examples for suitable radioactive detectable markers comprise $^{11}C$, $^{40}K$, $^{13}N$, $^{15}O$, $^{18}F$, $^{75}Br$, $^{76}Br$, $^{82}Rb$, $^{68}Ga$, $^{64}Cu$, $^{62}Cu$, $^{123}I$, $^{124}I$, $^{125}I$, $^{131}I$, $^{210}At$, $^{211}At$ and $^{111}In$, however are not limited thereto. Further examples for detectable markers relate to any atom or molecule that contributes to the provision of a detectable, preferably quantifiable, effect and which can be attached to a particle and/or a first molecule. A non-limiting list of these markers comprises for instance enzymes that generate a detectable signal, such as by means of colorimetry, fluorescence or luminescence. Examples of such enzymes comprise horseradish peroxidase, alkaline phosphatase, (beta)galactosidase or glucose-6-phosphate-dehydrogenase, chromophores, such as fluorescent, luminescent or common color compositions, groups with an electron density being detectable by electron microscopy or by means of the electric characteristics, such as conductivity, amperometry, voltammetry or impedance. Preferably the detectable marker is a luminescent marker and/or a fluorescence marker. Further preferred the detectable marker is a fluorescence marker.

Thus the oligomers of the oligomer array in the respective terminal position each comprise a detectable marker. The presence of the detectable marker can be of value for the investigation of the oligomers, or the binding behavior thereof, respectively, to a binding partner. For instance by the effected binding of a binding partner to a particular oligomer the signal of the detectable marker thereof may be (partially) erased, whereby the detection of the binding occurrence is made possible.

In one embodiment only one particle fits into one recess. Thus it can be ensured that only the molecule type, that is contained within the particle, can react. More preferred the molecule type is a defined molecule and not a mixture of different molecules.

In one embodiment the oligomer array according to the invention is used for determining a binding partner.

The binding partner preferably is a medically or diagnostically usable molecule.

DNA/RNA strands can be utilized for binding their complementary strand or strands respectively, and small molecules for binding antibodies. Other non-limiting examples comprise enzymes, antibodies, conjugated enzymes, conjugated antibodies, glycoproteins, deoxyribonucleic acid molecules, deoxyribonucleic acid fragments (oligomers), polymer molecules, ribonucleic acids, ribonucleic acid fragments, pharmaceuticals, aptamers, hormones and/or combinations thereof.

In one embodiment a particle with a molecule is provided, wherein at least one of the particle and/or of the molecule comprises a detectable marker. The first molecule herein resides within the first particle.

The stochastic oligomer arrays described in the present application differ from the oligomer arrays and in particular with respect to the peptide arrays that could be produced before in the very first in the number of different oligomers that can be synthesized thereby in array format. Using a pitch of 2 µm (25 million spots/cm$^2$) and a size of an object slider of about 15 cm$^2$ the present method results about 1 billion peptide spots. Such large peptide variations that can be reached using the stochastic oligomer arrays according to the invention up to now only were reached using the phage-display method so that these can be used for typical high throughput screening methods, in particular when there is no initial information with respect to the molecule to be investigated (e.g. the search for a binding partner to oligomers). A major technical advantage of the invention rests in the fact of a significant increase in the spot density and the very high spot number on the carrier resulting therefrom. Since the costs of synthesized arrays depend substantially from the surface, whereon they are synthesized, when compared with other synthesis methods this leads to a very high cost advantage per synthesized oligomer and in particular peptide. A positioning technique precise on micrometer of even nanometer scale is not necessary, while the other methods according to the prior art require cost intensive, maintenance intensive and damage prone devices, such as for instance lithography masks, printers and similar devices. A further advantage of the method rests in the fact that the present method can be easily scaled. Namely there is only a small additional effort, if instead of a substrate with a smaller surface a larger surface or already several substrates shall be provided with oligomers. By adapting the particle size to the size of the recesses the spot density can in addition be increased to 100 million spots/cm$^2$ which exceeds the (array) technique according to the prior art by 3 to 5 magnitudes. With the currently available fluorescent methods for detecting single molecules or monomers of the oligomers, respectively, it is possible to even detect single colorant molecules. With the stochastic oligomer arrays at the first time a full combinatorics with amino acid components is made possible. To fully exploit the complete combinatorics of a 5-mer peptide 3.2 million spots are necessary, with a 6-mer 64 million spots are necessary and with a 7-mer peptides 1.28 billion spots are necessary. A further advantage—when compared to bioxerographic methods according to the prior art—rests in the simplified composition of the particles. The particles must not have any electric charge or comprise charge generating and charge stabilizing additives, since one does not rely on the manipulation of the particles with electric fields.

By the method according to the invention so-called focused libraries can be provided particularly simply. If for instance a peptide binder to an antibody or to a target protein is searched that can be switched by heat, then amino acid positions that are responsible for the binding to the antibody or to the target protein can be kept constant, while the positions that are rather unimportant for the binding, can be varied, or permutated, respectively. Thereafter the binding of the target protein to the respective peptide variants can be checked at different temperatures, to find out whether in this way possibly an entropy driven and thereby temperature-dependent variant of the originally found peptide can be found.

By the method according to the invention all kinds of special components can be built into the oligomers, in particular into the peptides. This can be done either directly during the peptide synthesis, or also after the synthesis has done, e.g. by a click reaction. The latter in particular is important, if the special component does not endure the conditions during synthesis (commonly 50% TFA during dividing of the peptides; 20% piperidine in DMF), i.e. the special component decomposes or undergoes a reaction, respectively. The special components may have all kinds of functions. Porphyrin derivates and ferrocenes can harvest light or can convey electrons. Other special components may have magnetic characteristics or may alter their molecule structure possibly reversibly by irradiation of light. Still further components may effect a circularization of the peptides, e.g. via alkyne and azide functions after adding a catalyst.

Many antibodies recognize short fragments of 5-15 amino acids, wherein 3 to 7 of the amino acids within the peptide are responsible for the specifity of the binding. This means that the specifity of the binding to the (linear) antigen with almost any monoclonal antibody can be easily determined if only a sufficient number of randomly produced peptides are colored therewith in array format, without any initial information being necessary therefore. In a subsequent experiment then thereafter some of the peptides found in this way can be varied systematically to determine the so-called binding signature, i.e. the amino acid positions which are responsible for the specifity of the binding. Using this information thereafter within the data bases it can looked for suitable candidate antigens that have initially induced this antibody. The human proteome can be represented by about 12 million different peptides. Using a stochastic peptide array it is possible to image the total human proteome on an object slider and to capture same in total in one experiment.

Using the described method according to the invention it is made possible to simply determine the binding epitopes with antibodies to recognize the conformational epitopes. Usually this consists of two peptide ring closures on the surface of the protein that are together recognized by the antibody. Linear peptides cannot reproduce this "loop character", since these have many different folding possibilities which goes at the expense of binding affinity. By producing a large number of different circular peptides it is possible to find a circular peptide that replicates such a ring closure. As described above then thereafter the binding signature can be determined and within the data bases it can be searched for candidate antigens (in particular if two different peptide ring closures fit one protein).

However, such a method cannot only be used for characterizing monoclonal antibodies, but also for characterizing antibody mixtures, such as present within serums of patients. The present invention may allow the determination of several dozens up to several hundred different signatures (as described above) per patient serum, completely without any previous information and to search thereafter for correlations between the found antibodies and disease conditions.

In full analogy to the search for peptides that characterized antibodies, the method according to the invention allows also to search with circularized peptides for binders to therapeutically interesting target proteins. With linear peptides this is often impossible, since the (too) many folding possibilities of a linear peptide frequently influenced the binding affinity to a target protein of interest detrimentally.

The invention subsequently is described with reference to embodiments and more fully described within the subsequent description.

EXAMPLES

Example 1: Placing the Particles within the Recesses of a Substrate

In FIGS. 4 to 7 the filling of recesses on a substrate is illustrated. It can be seen that the filling degree of the recesses can be varied over a wide range as necessary, and that also the filling of the recesses is done stochastically.

Figure 4:
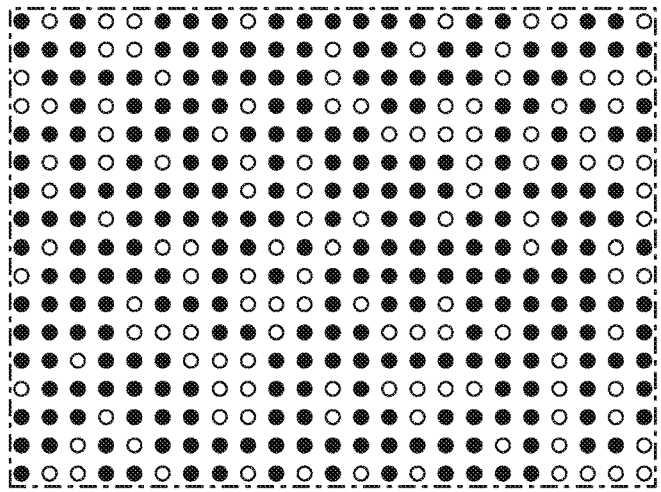
FIG. 4 shows a 60% filling of cylindrical recesses (diameter 5 µm, pitch 10 µm, depth 5 µm) using polymer particles (diameter 4 µm)

FIG. 4 shows a 60% filling of cylindrical recesses (diameter 5 μm, pitch 10 μm, depth 5 μm) with polymer particles (diameter 4 μm).

Figure 5:
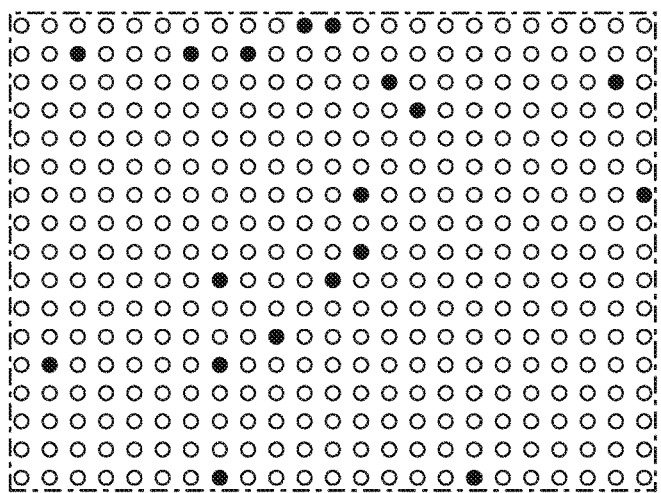
FIG. 5 shows a 5% filling of cylindrical recesses (diameter 6 µm, pitch 4 µm, depth 5 µm) with particles (diameter 4.21 µm). The particles were placed within the recesses in suspensions, the concentration of the suspension is 2 µl particles in 2.4 ml water.

In FIG. 5 a 5% filling of cylindrical recesses (diameter 6 μm, pitch 4 μm, depth 5 μm) with particles (diameter 4.21 μm) is shown. The particles were placed into the recesses within a suspension, the concentration of the suspension is 2 μl particles within 2.4 mL water.

Figure 6:
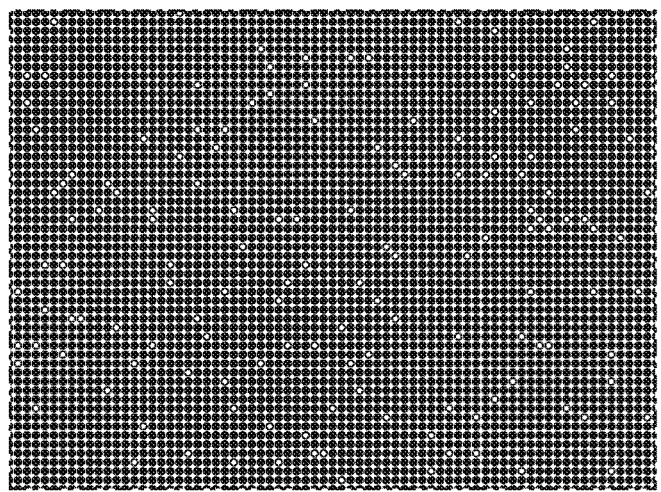
FIG. 6 shows a 6.4% filling of cylindrical recesses (diameter 0.6 µm, pitch 2 µm, depth 1 µm) with glycine amino acid particles. The particle pattern was produced by means of a roller.
Figure 10A:
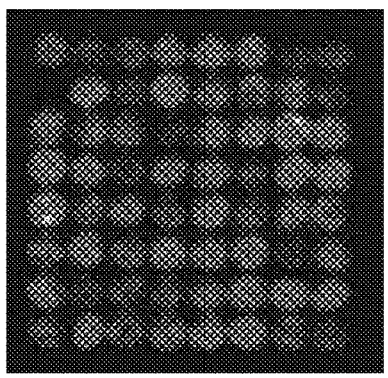
FIGS. 10a, 10b, 10c, 10d, 10e, 10f, 10g, 10h and 10i show the peptide array according to example 3. The respectively left image of FIGS. 10a to 10e shows each of the nine possible layers of the fluorescence picture. The right figure shows the amino acid pattern belonging to the respective layer.
Figure 10B:
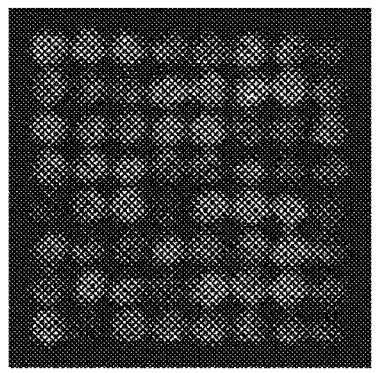
Figure 10C:
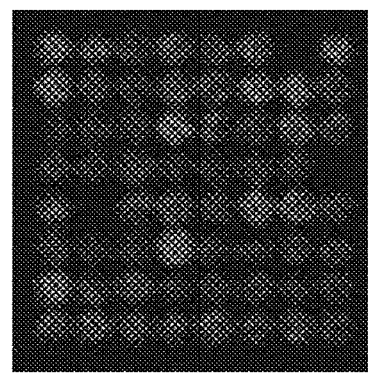
Figure 10D:
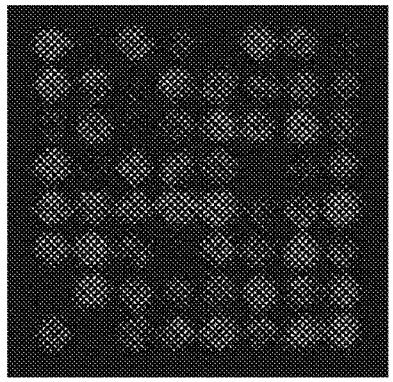
Figure 10E:
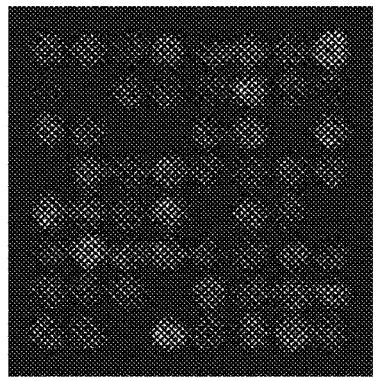
Figure 10F:
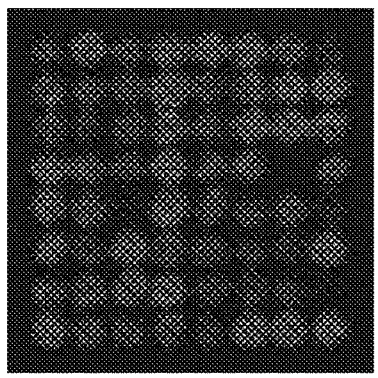
Figure 10G:
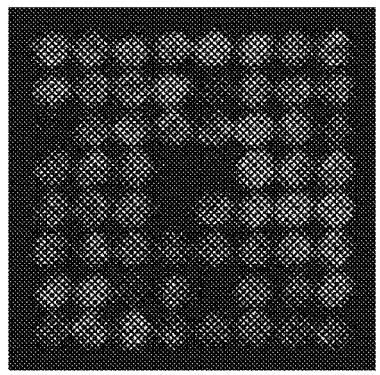
Figure 10H:
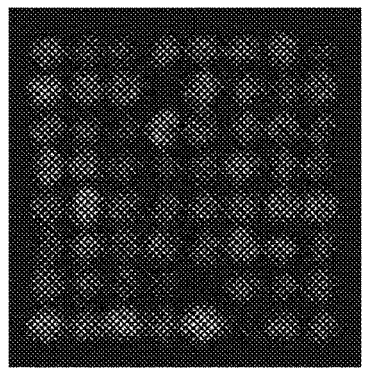
Figure 10I:
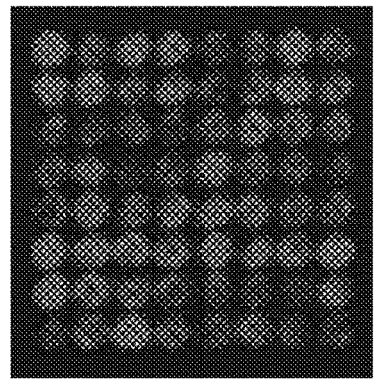

FIG. 6 shows a 6.4% filling of cylindrical recesses (diameter 0.6 μm, pitch 2 μm, depth 1 μm) with glycine amino acid particles. The particle pattern was produced by means of a roller.

In FIG. 7 an example for marking of monomer particles using fluorescent colorants is shown, light microscopy image (FIG. 7a) and fluorescence image of the randomly deposited particles (FIG. 7b). The location of the monomers is identified using fluorescence color (bright circles symbolize herein a red or green coloring, while the red coloring is somewhat brighter). Unfilled recesses are used for the deposition of subsequent monomers, pitch 10 μm.

Example 2: Production of a Dipeptide Array from Glycine and Biotin Monomers

Further details for the process and the materials and methods that are used can be taken from the subsequent example 3.

In a first step a suitable substrate is produced. A glass object slider with recesses of a diameter of 1 μm and a depth of 1 μm is provided. The pitch of the recesses is 2 μm. The surface of the substrate is thereafter provided with a poly (ethylene glycol) methacrylate graft layer, or a plug polymer layer (10:90 PEGMA-co-MMA polymer) and is thereafter functionalized using $NH_2$ groups to enable the peptide synthesis.

Glycine and OPfp activated biotin particles with a median diameter of 3 μm are produced from a styrene-acrylate copolymer as a matrix and respective monomers (glycine derivate and biotin) as described in WO 2014/169928 A1. The particles are placed within the recesses of the functionalized glass carrier by means of an elastic rubber roller, as shown schematically on the left side in FIG. 3. The position of the deposited glycine particles, or the biotin particles respectively, is determined by means of light microscopy images using a Leitz Ergolux 200. The used particles are produced by means of a spray-drying process and consist of the polymer matrix and the monomer derivative.

The binding to the amine functionalized surface of the substrate occurs at 90° C. for 90 minutes under argon atmosphere in a preheated laboratory furnace (supplier Nabertherm). Herein the substrate rests within a small metal box which is filled with argon. The amino acid derivatives in the matrix diffuse within this time to the substrate and bind there by forming an amide binding to the $NH_2$ groups present there in functionalized form.

The substrate then undergoes a washing step to remove the copolymer matrix, excess monomers and other components. Initially the substrate surface is rinsed for a long time with acetone and inserted into an ultrasonic bath using acetone for 5 minutes at a frequency of 132 kHz and a power of about 27 W (30% of the effective power of 80%). Thereafter there is a three-fold rinsing for 5 minutes with DMF and for 3 minutes a two-fold rinsing with MeOH. The individual washing steps are controlled using light microscopy.

Free amino groups on the surface of the substrate are blocked (acetylated). The blocking occurs over night using acetic anhydride-diisopropylethylamine-dimethyl formamide (ESA-DIPEA-DMF) at a ratio of 1:2:7. Thereafter it is rinsed three times with DMF (5 minutes) and two times with MeOH (3 minutes), and the substrate is dried within an argon stream.

Protective removing of the amino acids (removal of Fmoc at the N-terminals of the amino acids) is done with piperidine (20 vol.-%) in DMF for 20 minutes, three-fold washing with DMF (for 5 minutes) and two-fold washing with MeOH (for 3 minutes). The substrate is dried under argon stream.

Thereafter again glycine amino acid particles for forming the second layer are applied.

The position of the deposited glycine particles is determined using light microscopy and pictures are taken.

Thereafter the deposition of biotin particles also on the second layer occurs.

The position of the deposited biotin particles is determined using light microscopy and a picture of the substrate is taken.

The coupling steps of the glycine derivate and biotin are performed as described above at 90° C. for 90 minutes under argon atmosphere.

The substrate subsequently is washed, free groups are blocked, and Fmoc groups are removed for protective removing of the amino acids.

Thereafter the substrate is washed with PBS-T buffer at a pH of 7.4 (one liter Millipore water, 500 μL Tween 20, 500 mg $NaN_3$) for 15 minutes.

The following combinations can be observed on the substrate: biotin, glycine-glycine, glycine-biotin. For controlling the synthesis products the carrier thereafter is colored with fluorescence marker (NHS-ester activation; red, binding to the free amino group of glycine) and with fluorescence marked streptavidin (green, binding to biotin). Herein the glycine-glycine spots have red signals and the spots with biotin, or glycine-biotin, respectively, have green signals. Other spots that do not carry the mentioned variants do not have fluorescence signals, as expected. A fluorescence image of the stochastic dipeptide array is shown in FIG. 8. FIG. 9 shows exemplarily 25 structures after the stochastic deposition of the two monomers in each of the two layers. FIG. 9a (glycine 1) and FIG. 9b (biotin 1) show the selected cutout after the stochastic deposition of the respective monomer of the first layer. FIG. 9c (glycine 2) and FIG. 9d (biotin 2) show the depositions of the second layer. A fluorescence image after the coloring of the synthesized array is shown in FIG. 9e. For assigning the individual structures they are numbered beginning with 1 (top left) to 25 (bottom right) (FIG. 9f). The fluorescence image after the coloring of the synthesized array is also shown. The evaluation of the occupation of the individual layers as well as the verification of the fluorescence image (table 1) shows the correspondence of the detected occupation with the expected fluorescence signals. The + symbolizes herein the detection of the respective component within the investigated structure.

TABLE 1

Dipeptide Synthesis

| Number | Fmoc-Glycine-OPfp 1 | Biotin 1 | Fmoc-Glycine-OPfp 2 | Biotin 2 | Color (theory) | Color (reality) |
|---|---|---|---|---|---|---|
| 1 |   |   |   | + | black | black |
| 2 |   |   |   |   | black | black |
| 3 |   |   |   | + | black | black |
| 4 | + |   |   |   | black | black |
| 5 |   |   |   | + | black | black |
| 6 |   |   |   |   | black | black |
| 7 |   | + | + |   | green | green |
| 8 |   |   |   |   | black | black |
| 9 |   |   |   |   | black | black |
| 10 |   |   |   |   | black | black |
| 11 |   |   |   |   | black | black |
| 12 |   | + |   | + | green | green |
| 13 |   |   |   |   | black | black |
| 14 |   |   |   |   | black | black |
| 15 |   |   |   |   | black | black |
| 16 |   |   | + |   | black | black |
| 17 |   | + |   |   | black | black |
| 18 |   |   | + |   | black | black |
| 19 |   |   |   | + | black | black |
| 20 |   |   |   |   | black | black |
| 21 |   | + |   |   | black | black |
| 22 |   |   |   |   | black | black |
| 23 |   |   |   | + | black | black |
| 24 | + |   | + |   | red | red |
| 25 |   | + |   |   | green | green |

In total the example 2 according to the invention shows that with the present method peptides can be generated that are arranged within the recesses of the substrate. The solid-phase synthesis used herein with particles with the molecule actually to be placed allows an easy production of longer oligomers, for instance polymers with a length of 15 amino acids, or amino acid derivatives, respectively, or more, by the targeted and selective placement of particular molecules to the reaction location. Thus the presented method opens an easy option for producing stochastic peptide arrays at a density of up to 70 million spots/cm$^2$. The skilled person is aware that the method described herein can be easily applied to the production of nucleotide arrays and/or other oligomer arrays, and that the here presented oligomer arrays can be used for detecting suitable binding partners within analytics.

Example 3: Production of a Peptide Array with Peptides of a Length of Up to 9 Amino Acids A stochastic peptide array with peptides of a length of up to 9 amino acids is produced. The successful synthesis of the peptide arrays is performed by means of coloring with fluorescence-marked antibodies including subsequent fluorescence screening.

3.1. Functionalizing the Substrate with Recesses

For the peptide array synthesis there is used a quartz glass object carrier with recesses having the dimensions 20 mm×20 mm×0.5 mm. The surface with the recesses has a pitch of 15 μm, a depth diameter of 12 μm and a depth of the recesses of 10 μm.

Before the production of the actual peptide arrays the object carrier is functionalized with a polymer layer from 10:90 PEGMA-co-MMA (poly(ethyleneglycol)methacrylate-co-methylmethacrylate).

3.2. Production of the Particles

Six kinds of particle types with different amino acids and quantum dot markings are synthesized before producing the stochastic peptide array. The amino acids as well as the markings for the individual particles are given in subsequent table 1.

TABLE 1

| No. | Fmoc-amino acid-OPfp | 1 letter code | Quantum dot marker |
|---|---|---|---|
| 1. | Alanine | A | 500 nm ("blue") |
| 2. | Asparagine acid | D | 500 nm ("blue") |
| 3. | Lysine | K | 590 nm ("green") |
| 4. | Proline | P | 590 nm ("green") |
| 5. | Tyrosine | Y | 590 nm ("green") |
| 6. | Valine | V | 590 nm ("green") |

3.2.1 Materials

1. Solid carrier powder: quasi-monodisperse microparticles based on side-linked PMMA with a median diameter of 10 μm.
2. Polymer matrix: styrole acryle copolymer.
3. Amino acid: powder of the Fmoc, OPfp-protected amino acid.
4. Solution of quantum dots (QD): 25 mg QD within 4 ml chloroform.
5. Dichloromethane (DCM).
6. Acetone.
7. Ethanol.

3.2.2 Implementation a) Preparation Steps 1 g of the solid carrier powder is introduced into the cup glass (25 ml). 0.1 g of the polymer matrix and 0.01 g of the amino acid powder are introduced into a jar 1. 50 μl QD-solution in chloroform are introduced into the jar 2. 2 ml DCM are added to the jar 2. It is waited, until the QDs are dissolved in DCM. 30 ml of acetone are input into the calibration burette.

b) Marking of the Solid Carrier 8 ml of DCM are given into the cup glass with the solid carrier powder and are stirred using a magnetic stirrer, until a homogeneous dispersion is obtained. 2 ml of the QD-solution from the jar 2 are given into the cup glass with the solid carrier dispersion. While stirring the solid carrier in DCM, slowly 30 ml of acetone are added from the burette to the dispersion over a time of 1 to 1.5 hours. Thereafter the stirring ends and it is waited for the sedimentation of the solid carrier particles, or a centrifuge is used, respectively. The liquid phase of the dispersion is removed, whereby the solid carrier particles remain into the cup glass. 15 ml of ethanol are given into the calibration burette and added to the cup glass with the solid carrier particles while stirring over a time of 10 to 15 minutes. The stirring ends and it is waited for the sedimentation of the solid carrier particles, or a centrifuge is used. The liquid phase of the dispersion is removed while keeping the solid carrier particles within the cup glass.

c) Washing the Solid Carrier 10 ml of acetone are given into the cup glass with the solid carrier. The dispersion is stirred for 1 minute. After ending the stirring process it is waited for the sedimentation of the solid carrier particles, or the centrifuge is used, respectively. The liquid phase of the dispersion is removed, while keeping the solid carrier particles within the cup glass.

d) Amino Acid Polymer Matrix Application 4 ml of DCM are given into the jar 1. It is waited until the polymer matrix and the amino acid powder have dissolved.

4 ml of the solution from the jar 1 are added to the cup glass with the solid carrier. It is stirred, until a homogeneous dispersion is obtained, and it is waited until a homogeneous mass emerges due to the evaporation of DCM from the dispersion. The residual is left for 2 hours to fully dry.

3.3 Peptide Array Synthesis

The synthesis of the stochastic peptide arrays usually comprises the following steps:

Fmoc—deprotecting the terminal $NH_2$-groups of the polymer chains, or amino acid chain(s), respectively.

Introducing the particle mixture into the recesses of the microstructured substrate corresponding to the desired amino acid deposition per layer.

Checking the substrate for deposited particles while using a fluorescence scanner to determine the position of quantum dot marked particles.

Decoding the fluorescence pattern into the respective amino acid pattern.

Extracting and binding the amino acids.

Removing the particles and washing out the residuals after the binding.

Acetylating (blocking) of non-reacted free terminal $NH_2$-groups.

The sequence of these method steps is repeated nine times, each time for the respective amino acid layer. At each amino acid layer possibly present side-chain functionalities are protected, and after effecting the synthesis of all amino acid layers the side-chain functionalities are deprotected.

The kinds of amino acids for each cyclus are selected so that the FLAG and HA-epitopes can be produced with sufficient probability by random synthesis. The particle mixtures that are used for each peptide array layer are shown in the subsequent table 2.

TABLE 2

| Layer no. | Particle type 1 | | Particle type 2 | |
|---|---|---|---|---|
| | Fmoc-amino acid-OPfp | Fluorescence marker | Fmoc-amino acid-OPfp | Quantum dot marker |
| 1. | Alanine (A) | 500 nm ("blue") | Lysine (K) | 590 nm ("green") |
| 2. | Asparagine acid (D) | 500 nm ("blue") | Tyrosine (Y) | 590 nm ("green") |
| 3. | Asparagine acid (D) | 500 nm ("blue") | Asparagine acid (D) | 500 nm ("blue") |
| 4. | Asparagine acid (D) | 500 nm ("blue") | Proline (P) | 590 nm ("green") |
| 5. | Asparagine acid (D) | 500 nm ("blue") | Valine (V) | 590 nm ("green") |
| 6. | Asparagine acid (D) | 500 nm ("blue") | Lysine (K) | 590 nm ("green") |
| 7. | Tyrosine (Y) | 590 nm ("green") | Tyrosine (Y) | 590 nm ("green") |
| 8. | Asparagine acid (D) | 500 nm ("blue") | Proline (P) | 590 nm ("green") |
| 9. | Tyrosine (Y) | 590 nm ("green") | Tyrosine (Y) | 590 nm ("green") |

The production of the peptide array is performed in the following way.

3.3.1 Fmoc-Deprotecting the $NH_2$-Groups

One-time swelling of the polymer layer from 10:90 PEGMA-co-MMA in dimethylformamide (DMF) for 5 minutes. One-time deprotecting of the terminal $NH_2$-groups using a solution of piperidine (20 vol.-%) and DMF (80 vol.-%) for 30 minutes. Two-fold washing of the substrate with DMF for 5 minutes. Two-fold washing of the substrate with methanol for 2 minutes. One-time rinsing of the substrate with dichloromethane (DCM) for 30 seconds. Drying the substrate with argon.

3.3.2 Initial Fluorescence Scanning

The substrate is checked while using a fluorescence scanner InnoScan1100 AL to determine the fluorescence pattern of the empty substrate.

3.3.3 Deposition of the Particles

The recesses of the substrate are filled with a powder mixture of particles. Particles not present within the recesses are removed while using pressurized air. The particle deposition within the recesses is checked using an optical microscope. In case of a low filling rate the afore-mentioned steps 3 are repeated.

3.3.4 Verification of Particles

The substrate is checked while using a fluorescence scanner InnoScan1100 AL to determine the fluorescence pattern of the particles deposited within the recesses.

3.3.5 Amino Acid Extraction and Binding Step

The substrate is transferred into a binding chamber. Herein the binding chamber must only allow an airtight closure of the substrate and must be sufficiently temperature resistant to allow a heating of the substrate. The chamber is filled with argon. Extraction and binding of the amino acid molecules to the terminal $NH_2$-groups of PEGMA-10/90-layer/peptide chains is performed within a furnace at 90° C. for a time of 60 minutes. Thereafter it is waited for 30 minutes for cooling of the chamber.

3.3.6 Removing the Particles and Washing the Substrate

One-time washing of the substrate with acetone for 2 minutes. One-time washing of the substrate with acetone for 2 minutes with an ultrasonic bath. One-time washing of the substrate with acetone for 2 minutes. Cleaning the substrate with air.

3.3.7 Blocking Step

One-time swelling of the polymer layer of 10:90 PEGMA-co-MMA in DMF for 5 minutes. One-time blocking of free $NH_2$-groups on the substrate with a solution of acetic acid anhydride (10 vol.-%), diisopropylethylamine (DIPEA) (20 vol.-%) and DMF (70 vol.-%) for 10 minutes. One-time blocking of remaining free $NH_2$-groups on the substrate with the solution of acetic acid anhydride (10 vol.-%), DIPEA (20 vol.-%) and DMF (70 vol.-%) for 30 minutes. Two-fold washing of the substrate with DMF for 5 minutes. Two-fold washing of the substrate with methanol for 2 minutes. One-time rinsing of the substrate with DCM for 15 seconds. Drying of the substrate with argon.

3.3.8 Storing the Substrate Over Night

The substrate, i.e. the quartz glass object carrier with the recesses, is placed within a storage box for object carriers. The storage box is filled with argon, is closed with paraffin and stored within a fridge at 4° C.

3.4. Decoding the Fluorescence Pattern

The fluorescence pattern is obtained for each of the nine layers of the peptide array while using a fluorescence scanner InnoScan1100 AL (Innopsys). Thereafter the respective amino acid pattern form the fluorescence images are decoded. This is shown in den FIGS. 10a to 10e for each of the layers 1 to 9, wherein the left image shows the fluorescence image and the right image shows the respective amino acid pattern of the respective layer. The entirety of the information of FIG. 10a to e is the 3D deposition mask, i.e. the full information on the synthesis location (the coordinate of the recess) of a peptide on the carrier and the sequence of the amino acids of the respective peptide.

3.5. Identifying the Peptides within the Array

On the basis of the results of the decoding of the amino acids, as described under 4, the synthesized peptide chains are identified. This is shown in the subsequent table 3.

TABLE 1

| Row | Column |  |  |  |  |  |  |  |
|---|---|---|---|---|---|---|---|---|
|  | 1 | 2 | 3 | 4 | 5 | 6 | 7 | 8 |
| 1 | AYDDDAYDPD DYPY | AYDDVKYDPV KYPY | KDD KYPY | KDDDD DYPY | KDDDD DYDY | AY | ADDPV KYPY |  |
| 2 |  | KDDP | ADDPVKDDDV KYPY DY | ADDPDKYDPD DYDY DYPY | AYDPV DYPY | AYDPV KYPY |  |  |
| 3 | KDDDDAYDPV D | KYDD KYDY | ADDP | AYDDVKDDDV DYDY DYPY | KDDP | KYDDV DYPY |  |  |
| 4 | KYDD DYDY | AYDPD DYDY | AYDDDKDDPV K | ADDPVAYD K | KDDPVKY |  |  |  |
| 5 | KDDDDKY KYPY |  | KYDDVADDDD KYDY D | KYDD DYPY | AYDDV | KYDPVKDDD DYDY |  |  |
| 6 | AYDDDKDDDD KYPY DYDY | AYDDVKDD KYPY |  | ADDDVKYDDV DYPY KYPY | ADDPDADDDV KYDY DYPY |  |  |  |
| 7 | ADD DYDY | AYDDD KYPY | KDDPV KDDP |  | KDDDVKYDPD K | KYDDDKYDDD KYDY DYPY |  |  |
| 8 | ADDPVKDD DYDY | KYDD | KYDDV KYDY | KYDDVKYDDV DYDY KYPY | KDDDDADDDD KYDY DYPY |  |  |  |

\* Amino acid sequences: from C-terminus (left) to N-terminus

From table 3 it can be seen that the Flag-epitope ((C-terminus)KDDDKYD-(N-terminus)) and the HA-epitope ((C-terminus)-AYDPVDYPY-(N-terminus)) are stochastically synthesized within the recesses (column 7, row 8 and column 7, row 2), respectively. It should be noted that the peptide chains in the specific recess are not elongated by further amino acids, in case the recess is not filled with a particle in the subsequent particle deposition step.

3.6. Incubation of the Peptide Array with Antibodies

Anti-HA- and anti-FLAG antibodies that are marked with fluorescent groups are used for verification. The anti-FLAG antibody is conjugated with the Cy5-colorant (red channel). The anti-HA-antibody is conjugated with the Cy3-colorant (green channel).

The incubation step is performed as shown the following.

Before a coloring the Fmoc and the side chain protective groups of the synthesized peptides must be removed. For coloring the peptide arrays the array is washed once with PBS for 15 minutes. The substrate surface is blocked once using Rockland buffer for 30 minutes. Three-fold washing of the substrate with a solution of PBS (90 vol.-%) and Rockland buffer (10 vol.-%) for 3 minutes. Incubation of the peptide array with a solution of PBS (2 ml), Rockland buffer (0.2 ml), anti-HA-antibody (2 µl) and anti-Flag-antibody (2 µl) for 2 hours. Five-fold washing of the peptide array with a solution of PBS (90 vol.-%) and Rockland buffer (10 vol.-%) for 2 minutes. Once rinsing the peptide array using Tris buffer (pH~7) for 15 seconds.

3.7. Fluorescence Checking

After the incubation the peptide array is checked using the afore-mentioned fluorescence scanner InnoScan1100 AL (Innopsys). The fluorescence image (FIG. 11) obtained thereby shows the fluorescence pattern of the incubated stochastic peptide array, wherein a coordinate system for simplification of the image analysis is provided.

3.8. Result

Figure 12:
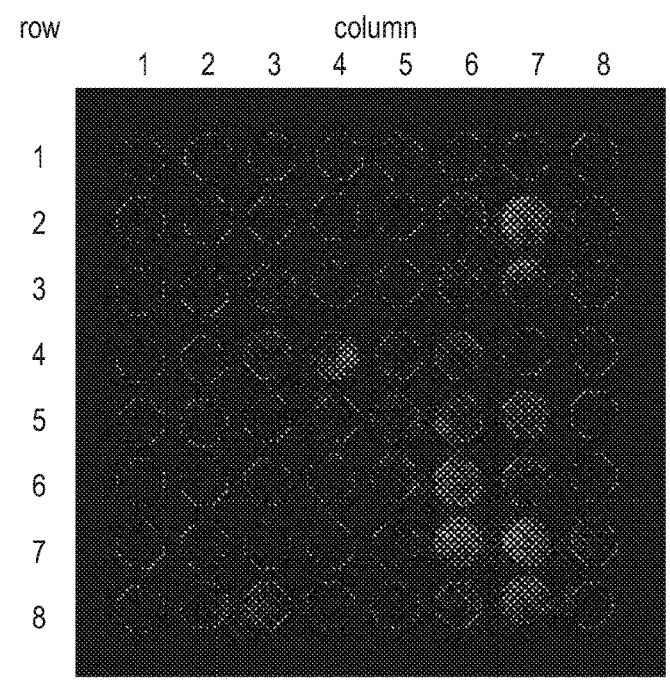
FIG. 12 shows the process image of the fluorescence pattern of the stochastical arrays incubated with anti-HA and anti FLAG antibodies.

After the image processing is completed, the fluorescence signals are assigned to the respective recesses of the substrate (FIG. 12). FIG. 12 shows the processed image of the fluorescence patterns of the incubated stochastic array, wherein a coordinate system for simplifying the image analysis is provided.

Figure 11:
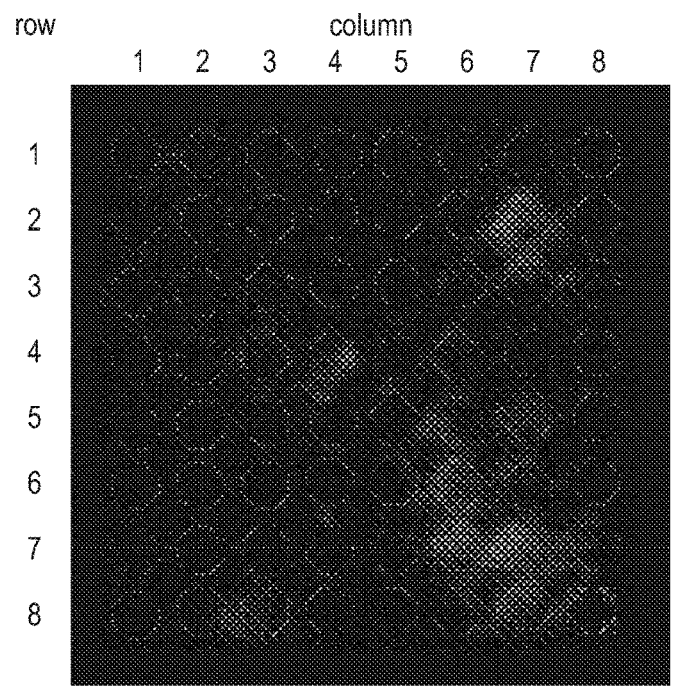
FIG. 11 shows the fluorescence pattern of the stochastical peptide arrays from example 3 incubated with the anti-HA and anti FLAG antibodies.

As can be seen from FIGS. 11 and 12, the peptide array is successfully produced using the stochastic method according to the invention. The desired peptide chains were fully synthesized, as is shown by successful fluorescence marking for determining the respective fluorescence marking.

The strongest signal within the green channel (which is provided by the anti-HA-antibody that is conjugated with the CY3-colorant) corresponds to the stochastically synthesized HA-epitope.

The FLAG-epitope, as well as several peptides, that have the fragment of the amino acid sequence *KYD**K/D* show strong signals within the red channel (which are caused by the anti-flag-antibody that is conjugated with the CY5-colorant).

What is claimed is:

1. A method of producing an oligomer array, comprising:
   (a) providing a substrate with a plurality of recesses;
   (b) stochastically placing a first particle with a first molecule within a recess, wherein a plurality of first particles are respectively placed in different recesses of the substrate without determining in advance which particle will be placed at which location of the array;
   (c) releasing the first molecule from the first particle;
   (d) binding the first molecule to a second molecule while forming an oligomer, wherein the second molecule is immobilized within the recess;
   (e) repeating (b) to (d) while elongating the oligomer; wherein at least a first particle comprises a detectable marker.

2. The method of claim 1, wherein the first molecule is an amino acid.

3. The method of claim 1, wherein after step (b) a determination of the detectable marker is performed in dependence on a position of the recess on the oligomer array.

4. The method of claim 1, further comprising generating a 3D deposition mask as step (f) from a determination of the detectable marker in dependence of a position of the recess on the oligomer array.

5. The method of claim 1, wherein after step (d) a chemical modification of the immobilized oligomer is performed, whereby a chemically modified oligomer is obtained.

6. The method of claim 1, wherein the detectable marker is a removable, detectable marker that is detectable by light microscopy.

7. The method of claim 1, wherein the first particle comprises a polymer matrix within which the first molecule is embedded.

8. The method of claim 1, wherein in step (b) the placing of a single first particle is done with a first molecule in a single recess.

9. The method of claim 1, wherein a surface functionality on lands between individual recesses is chemically modified.

10. The method of claim 1, wherein at least one recess is sealed during step (c) and step (d).

11. The method of claim 1, wherein synthesized oligomers are transferred onto a target surface, wherein the synthesized oligomers are fully synthesized oligomers.

12. The method of claim 1, wherein at least a first molecule comprises a detectable marker.

* * * * *